US006913882B2

(12) United States Patent
Glynne et al.

(10) Patent No.: US 6,913,882 B2
(45) Date of Patent: Jul. 5, 2005

(54) METHODS OF SCREENING FOR B CELL ACTIVITY MODULATORS

(75) Inventors: Richard Glynne, Palo Alto, CA (US); Chris Goodnow, Ainslie (AU); David Mack, Menlo Park, CA (US)

(73) Assignees: Affymetrix, Inc., Santa Clara, CA (US); Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 09/747,760

(22) Filed: Dec. 21, 2000

(65) Prior Publication Data

US 2001/0031462 A1 Oct. 18, 2001

Related U.S. Application Data

(60) Provisional application No. 60/171,796, filed on Dec. 22, 1999.

(51) Int. Cl.[7] .............................. C12Q 1/00; C12Q 1/70; C01N 33/543; C07H 21/04
(52) U.S. Cl. ........................... 435/6; 435/7.1; 435/91.1; 435/DIG. 2; 435/DIG. 14; 435/DIG. 17; 435/DIG. 40; 436/518; 536/23.1; 536/23.2
(58) Field of Search ...................... 435/6, 91.1, DIG. 2, 435/DIG. 14, DIG. 17, DIG. 40, 5, 7.1; 436/518; 536/23.1, 23.2

(56) References Cited

U.S. PATENT DOCUMENTS 5,580,722 A * 12/1996 Foulkes et al. ................. 435/6
6,110,666 A * 8/2000 Grosveld et al. .............. 435/6

FOREIGN PATENT DOCUMENTS

WO    WO97/10365 A1    3/1997
WO    WO97/27317 A1    7/1997

OTHER PUBLICATIONS

Cruse et al., Illustrated Dictionary of Immunology, 1995, pp. 56–59, CRC Press New York.*
Genbank Accession No.: AA017811, gene name: neurogranin.
Genbank Accession No.: AA106931, gene name: hiP30.
Genbank Accession No.: AA120620, gene name: CD83.
Genbank Accession No.: AA154742, gene name: BL34.
Genbank Accession No.: AF024519, gene name: GILZ.
Genbank Accession No.: AK017185, gene name: hRab30.
Genbank Accession No.: AK017885, gene name: hRhoH.
Genbank Accession No.: D00466, gene name: ApoE.
Genbank Accession No.: D26091, gene name: CDC47.
Genbank Accession No.: D28492, gene name: capspase 2.
Genbank Accession No.: D37797, gene name: RP105.
Genbank Accession No.: D38417, gene name: Ah–R.
Genbank Accession No.: D42124, gene name: mafk.
Genbank Accession No.: D63902, gene name: EFP.
Genbank Accession No.: D78141, gene name: TRAF5.
Adachi, Takahiro, et al.; Cutting Edge: The B Cell Surface Protein CD72 Recruits the Tyrosine Phosphatase SHP–1 upon Tyrosine Phosphorylation; *The Journal of Immunology*; 1998; pp. 4662–4665; vol. 160.
Alessi, Dario R. et al.; PD 098059 Is a Specific Inhibitor of the Activation of Mitogen–activated Protein Kinase Kinase in Vitro and in Vivo; *The Journal of Biological Chemistry*; Nov. 17, 1995; pp. 27489–27494; vol. 270, No. 46.
Cooke, Michael P., et al.; Immunoglobulin Signal Transduction Guides the Specificity of B Cell–T Cell Interactions and Is Blocked in Tolerant Self–reactive B Cells; *The Journal of Experimental Medicine*; Feb. 1994; pp. 425–438; vol. 179.
Dolmetsch, Ricardo E.; Differential activation of transcription factors induced by $CA^{2+}$ response amplitude and duration; *Nature*; Apr. 24, 1997; pp. 855–858; vol. 386.
Goodnow, Christopher C.; Self–Tolerance Checkpoints in B Lymphocyte Development; *Advances in Immunology*, 1995; pp. 279–368; vol. 59.
Grumont, Raelene J., et al.; Activation of the Mitogen–Activated Protein Kinase Pathway Induces Transcription of the *PAC–1* Phosphatase Gene; *Molecular and Cellular Biology*; Jun. 1996; pp. 2913–2921; vol. 16, No. 6.
Grument, Raelene J., et al.; Rel–dependent induction of *A1* transcription is required to protect B cells from antigen receptor ligation–induced apoptosis; *Genes & Development*; 1999; pp. 400–411; vol. 13.
Healy James I., et al; Different Nuclear Signals Are Activated by the B Cell Receptor during Positive Versus Negative Signaling; *Immunity*; Apr. 1997; pp. 419–428; vol. 6.
Healy James I., et al.; Quantitative and Qualitative control of antigen receptor signaling in tolerant B lymphocytes; *Immunological Tolerance*; Novartis Foundation Symposium 215; 1998; pp. 137–145; John Wiley & Sons; England.
Hong, Jin Xin, et al.; Isolation and Characterization of a Novel B Cell Activation Gene; *The Journal of Immunology*; May 1, 1993; pp. 3895–3904; vol. 150.
Huo, Li, et al.; Receptor–Specific Induction of Individual AP–1 Components in B Lymphocytes: *The Journal of Immunology*, 1995; pp. 3300–3309; vol. 154.

(Continued)

*Primary Examiner*—Padmashri Ponnaluri
(74) *Attorney, Agent, or Firm*—Townsend and Townsend and Crew, LLP

(57) ABSTRACT

The invention provides for the identification of all genes, whether known or novel, which are differentially expressed within and among B cells, making possible the characterization of their temporal regulation and function in the B cell response and/or in B cell mediated disorders. Expression profiles, nucleic acids and proteins are provided for differing states of B cells, including resting, naive, activated, tolerant and immunosuppressed B cells. The present invention makes possible the identification and characterization of targets useful in prognosis, diagnosis, monitoring, rational drug design, and/or therapeutic intervention of immune system disorders.

8 Claims, 5 Drawing Sheets

OTHER PUBLICATIONS

Iida, Shinsuke, et al.; Deregulation of MUM1/IRF4 by chromosomal translocation in multiple myeloma; *Nature Genetics*; Oct. 1997; pp. 226–230; vol. 17.

Kuo, Chay T., et al.; LKLF: A Transcriptional Regulator of Single–Positive T Cell Quiescence and Survival; *Science*; Sep. 26, 1997; pp. 1986–1990; vol. 277.

Langdon, Wallace Y., et al.; The c–*myc* Oncogene Perturbs B. Lymphocyte Development in Eμ–*myc* Transgenic Mice; *Cell*; Oct. 10, 1986; pp. 11–18; vol. 47.

Marton, Matthew J., et al; Drug target validation and identification of secondary drug target effects using DNA microarrays; *Nature Medicine*; Nov. 1998; pp. 1293–1301; vol. 4, No. 11.

Mason, David Y., Development and follicular localization of tolerant B lymphocytes in lysozyme/anti–lysozyme IgM/IgD transgenic mice; *International Immunology*; 1992; pp. 163–175; vol. 4, No. 2.

Mittelstadt, Paul R., et al.; Induction of Early Response Genes by Cross–Linking Membrane Ig on B Lymphocytes; *The Journal of Immunology*; Jun. 1, 1993; pp. 4822–4832; vol. 150.

Mittrücker, Hans–Willi, et al.; Requirement for the Transcription Factor LSIRF/IRF4 for Mature B and T Lymphocyte Function; *Science*; Jan. 24, 1997; pp. 540–543; vol. 275.

Monroe, John G.; Up–Regulation of c–*fos* Expression is a Component of the mIg Signal Transduction Mechanism but is not Indicative of Competence for Proliferation; *The Journal of Immunology*; Mar. 1, 1988; pp. 1454–1460; vol. 140.

Newton, Joshua S.; B cell early response gene expression coupled to B cell receptor, CD40 and interleukin–4 receptor co–stimulation: evidence for a role of the *egr–2/krox20* transcription factor in B cell proliferation; *Eur. J. Immunol*; 1996; pp. 811–816; vol. 26.

Pfisterer, Petra, et al.; CRIPS–3, a Protein with Homology to Plant Defense Proteins, Is Expressed in Mouse B Cells under the Control of Oct2; *Molecular and Cellular Biology* Nov. 1996; pp. 6160–6168; vol. 16, No. 11.

Rathmell, Jeffrey, et al.; Repression of B7.2 on Self–reactive B Cells Is Essential to Prevent Proliferation and Allow Fas–mediated Delection of CD4+ T Cells; Aug. 17, 1998; pp. 651–659; vol. 188, No. 4.

Seyfert, Vicki L.; Differential Expression of a Zinc Finger–Encoding Gene in Response to Positive versus Negative Signaling through Recepetor Immunoglobin in Murine B Lymphocytes; *Molecular and Cellular Biology*; May 1989; pp. 2083–2088; vol. 9, No. 5.

Slemmon, J. Randall, et al.; Camstatins Are Peptide Antagonists of Calmodulin Based Upon a Conserved Structural Motif in PEP–19, Neurogranin, and Neuromodulin; *The Journal of Biological Chemistry*; Jul. 5, 1996; pp. 15911–15917; vol. 271, No. 27.

Solvason, Nanette, et al.; Induction of Cell Cycle Regulatory Proteins in Anti–Immunoglobulin–stimulated Mature B Lymphocytes; *J. Exp. Med.*; Aug. 1996; pp. 407–417; vol. 184.

Svaren John, et al.; NAB2, a Corepressor of NGFI–A (Egr–1) and Krox20, Is Induced by Proliferative and Differentiative Stimuli; *Molecular and Cellular Biology*; Jul. 1996; pp. 3545–3553; vol. 16, No. 7.

Wicker, Linda S., et al.; Suppression of B cell activation by cyclosporin A, FK506 and rapamycin; *Eur. J. Immunol*; 1990; pp. 2277–2283; vol. 20.

\* cited by examiner

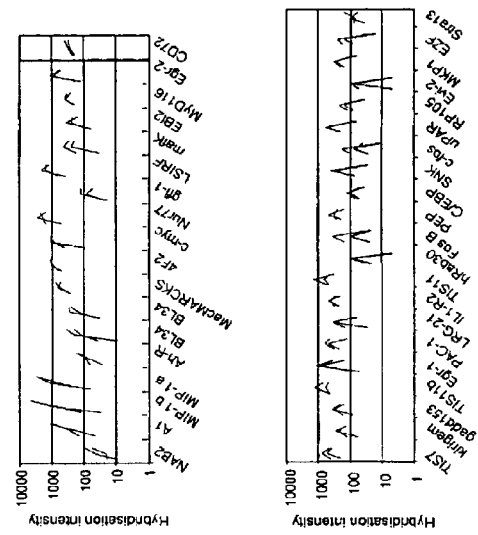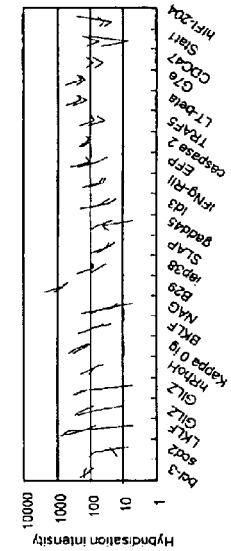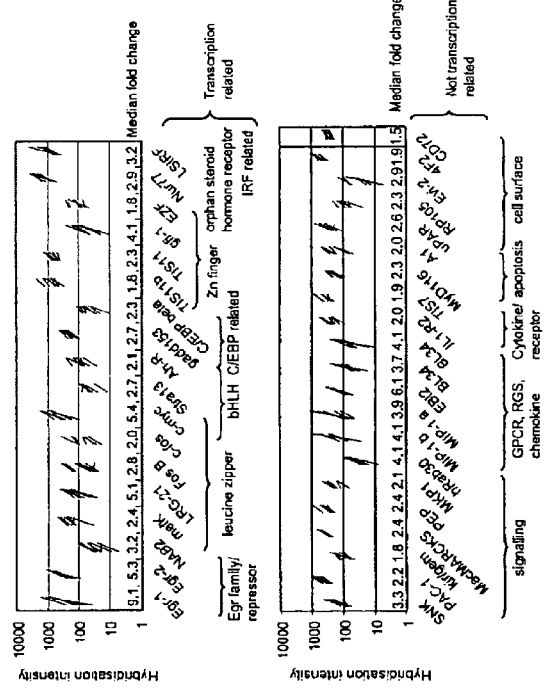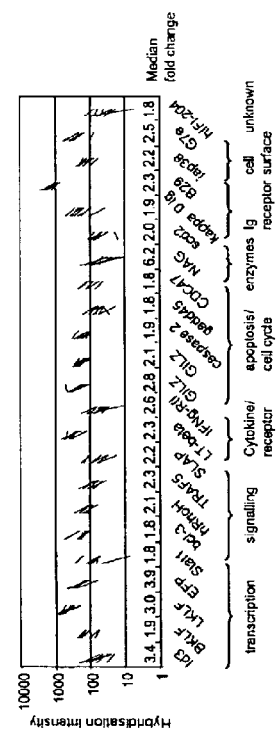

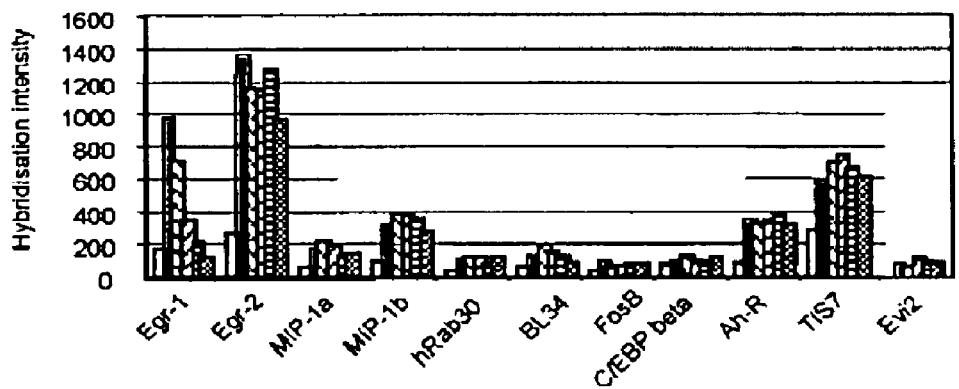
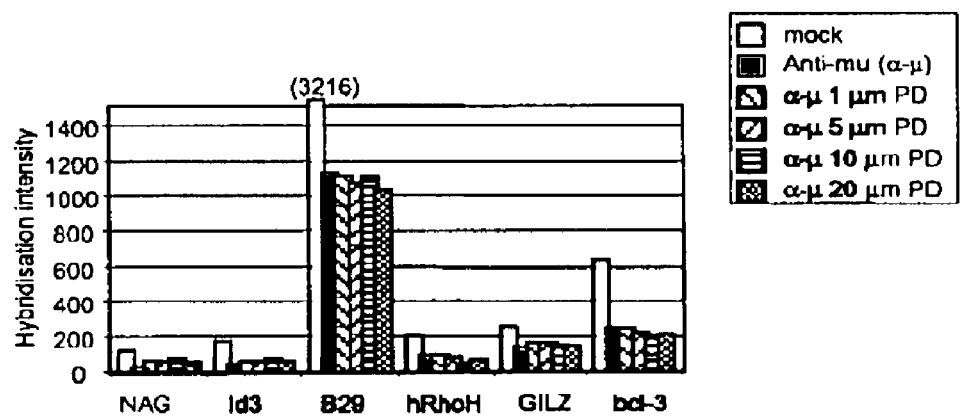
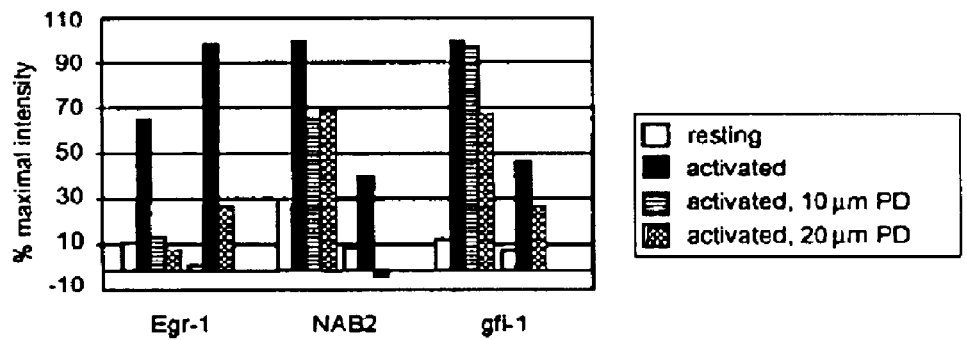
FIG. 3D

METHODS OF SCREENING FOR B CELL ACTIVITY MODULATORS

CROSS-REFERENCES TO RELATED APPLICATIONS

This application claims the benefit of U.S. Provisional Application No. 60/171,796, filed Dec. 22, 1999, which is incorporated herein by reference.

TECHNICAL FIELD

The invention relates to the identification of expression profiles and the nucleic acids involved in B cell activation, immunosuppression and immunological tolerance and to the use of such expression profiles and nucleic acids in methods for identifying candidate agents which modulate B cell activity.

BACKGROUND OF THE INVENTION

B lymphocytes (also referred to as B cells) mature within the bone marrow and leave the marrow expressing a unique antigen-binding membrane receptor. The B-cell receptor is a membrane-bound immunoglobulin glycoprotein. When a B cell encounters the antigen for which its membrane-bound antibody is specific, the cell begins to divide very rapidly; its progeny differentiate into memory B cells and effector cells called plasma cells. Memory B cells have a longer lifespan and continue to express membrane-bound antibody with the same specificity as the original parent cell. Plasma cells do not produce membrane-bound antibody but instead produce the antibody in a form that can be secreted.

Immunologic tolerance is a specific state of non-responsiveness to an antigen. Immunologic tolerance generally involves more than the absence of an immune response; this state is an adaptive response of the immune system, one meeting the criteria of antigen specificity and memory that are the hallmarks of any immune response. Tolerance develops more easily in fetal and neonatal animals than in adults, suggesting that immature T and B cells are more susceptible to the induction of tolerance. Moreover, studies have suggested that T cells and B cells differ in their susceptibility to tolerance induction. Induction of tolerance, generally, can be by clonal deletion or clonal anergy. In clonal deletion, immature lymphocytes are eliminated during maturation. In clonal anergy, mature lymphocytes present in the peripheral lymphoid organs become functionally inactivated.

Treatment of transplant and autoimmune patients often includes suppression of lymphocyte activation by tacrolimus (FKS506) or cyclosporin, both inhibitors of calcineurin. Borel, et al., (1976) *Agents Actions* 6: 468–75; Kino et al., (1987) *J. Antibiot.* (Tokyo) 40, 1256–65; Ho, et al, (1996) *Clin. Immunol. Immunopathol.* 80, S40–5; and Ruhlmann and Nordheim, (1997) *Immunobiology* 198, 192–206. While effective during therapy, these compounds do not allow (re-)establishment of immunological tolerance to the offending autoantigen and instead can inhibit tolerance induction. Prud'homme and Vanier, (1993) *Clin. Immunol. Immunopathol.* 66:185–92. Accordingly, the development of drugs that could induce tolerance would be desirable.

Therefore, it is an object of this invention to identify the expression profiles which are unique to B-cell tolerance, activation and immunosuppression. It is further an object to use the expression profiles in assays to identify agents which can be used in the modulation of B cell activity including B cell tolerance, activation, immunosuppression, mitosis, apoptosis, differentiation and migration. It is further an object to use the expression profiles as diagnostics to identify B cells which are abnormal. It is further an object to provide assays to identify agents for the treatment of B cell related disorders.

SUMMARY OF THE INVENTION

In one aspect of the invention, the identification of all genes, whether known or novel, which are differentially expressed within and among B cells are provided, making possible the characterization of their temporal regulation and function in the B cell response and/or in B cell mediated disorders. Thus, expression profiles, nucleic acids and proteins are provided for differing states of B cells, including resting, naïve, activated, tolerant and immunosuppressed B cells. Thus, the present invention makes possible the identification and characterization of targets useful in prognosis, diagnosis, monitoring, rational drug design, and/or therapeutic intervention of immune system disorders.

The invention provides methods of screening drug candidates. Such methods entail providing a cell that expresses an expression profile gene selected from the group Egr-1, Egr-2, Nur77, c-myc, MIP-1a, MIP-1b, BL34, gfi-1, NAB2, neurogranin, SLAP, A1, E2-20K, SATB1, Cctq, kappa V, pcp-4, TGIF, CD83, ApoE, Aeg-2, CD72, cyclin D2, 1ck, MEF-2C, bmk, IgD, Evi-2, vimentin, CD36, c-fes, c-fos, TRAP, hIP30, Ly6E.1, LRG-21, Fos B, gadd153, mafk, Ah-R, C/EBP beta, EZF, TIS7, TIS11, TIS11b, LSIRF, MKP1, PAC-1, PEP, MacMARCKS, SNK, Stra13, kir/gem, EB12, IL1-R2, MyD116, RP 105, uPAR, 4F2, hRab30, Id3, BKLF, LKLF, EFP, bcl-3, caspase 2, GILZ, hIFI-204, hRhoH, TRAF5, LT-beta, IFNg-RII, gadd45, CDC47, NAG, scd2, kappa 0 ig, iap38, G7e, B29, and SCD2. A drug candidate is added to the cell. The effect of the drug candidate on the expression of the expression profile gene is then determined.

In some methods the level of expression in the absence of the drug candidate to the level of expression in the presence of the drug candidate is compared. In other methods, the cell expresses an expression profile gene set of at least one expression profile gene, and the effect of the drug candidate on the expression of the set is determined. In some such methods, the profile gene set comprises a tolerance set comprising carb anh II, IgD, CD72, SATB1, ApoE, CD83, cyclin D2, Cctq, MEF-2C, TGIF, Aeg-2, Egr-1, 1ck, Egr-2, E2-20K, pcp-4, kappa V, neurogranin, NAB2, gfi-1 hIP-30, TRAP, bmk, CD36, Evi-2, vimetin, Ly6E.1, and c-fes. In some such methods, the expression of hIP-30, TRAP, bmk, CD36, Evi-2, and c-fes are decreased and the expression of carb anh II, CD72, SATB 1, ApoE, CD83, cyclin D2, Cctq, MEF-2C, TGIF, Aeg-2, Egr-1, 1ck, Egr-2, E2-20K, pcp-4, kappa V, neurogranin, NAB2, gfi-1 are increased as a result of the introduction of the drug candidate.

In some methods, the set comprises a stimulation set comprising Egr-1, Egr-2, NAB2, mafK, LRG-21, c-fos, c-myc, Stra13, AhR, gadd153, C/EBP beta, TIS11b, TIS11, gfi-1, EZF, Nur77, LSIRF, SNK, PAC-1, kir/gem, MacMARCKS, PEP, MKP 1, hRab30, MIP-1b, MIP-1a, EB12, BL34, IL1-R2, TIS7, MyD116, A1, uPAR, RP105, Evi-2 4F2, CD72, Id3, BKLF, LKLF, EFP, Stat1, bcl-3, hRhoH, TRAF5, SLAP, LT-beta, IFNg-RII, GILZ, Caspase 2, gadd45, CDC47, NAG, scd2, kappa 0 ig, B29, iap38, G7e, and hIFI-204. In some such methods, the expression of Id3, BKLF, LKLF, EFP, Stat1, bcl-3, hRhoH, TRAF5, SLAP, LT-beta, IFNg-RII, GILZ. Caspase 2, gadd45, CDC47, NAG, scd2, kappa 0 ig, B29, iap38, G7e, and hIFI-204 are decreased and the expression of Egr-1, Egr-2, NAB2, mafK, LRG-21, c-fos, c-myc, Stra13, AhR, gadd153, C/EBP beta, TIS11b, TIS11, gfi-1, EZF, Nur77, LSIRF, SNK, PAC-1, kir/gem, MacMARCKS, PEP, MKP1, hRab30, MIP-1b, MIP-1a, EB12, BL34, IL1-R2, TIS7, MyD116, A1, uPAR, RP105, Evi-2 4F2, CD72 are increased as a result of the introduction of the drug candidate.

In some methods, the set comprises an immunosuppression set comprising hIFI-204, hRhoH, caspase 2, B29, SLAP, NAG, iap38, gadd45, BKLF, G7e, Id3, scd2, GILZ, Stat1, kappa 0 ig, LT-beta, LKLF, IFNg-RII, mCDC47, EFP, TRAF5, and bcl-3. In some such methods, the immunosuppressive set further comprises c-fos, gadd153, EZF, C/EBP beta, Stra13, NAB2, mafK, and LRG-21. In some such methods the expression of c-fos, gadd153, EZF, C/EBP beta, Stra13, NAB2, mafK, and LRG-21 are increased as a result of the introduction of the drug candidate. In some methods the expression of hIFI-204, hRhoH, caspase 2, B29, SLAP, NAG, iap38, gadd45, BKLF, G7e, Id3, scd2, GILZ, Stat1, kappa 0 ig, LT-beta, LKLF, IFNg-RII, mCDC47, EFP, TRAF5, and bcl-3 are decreased and the expression of LSIRF, kir/gem, MKP1, hRab30, AhR, c-myc, Il1-R2, TIS11b,Evi-2, A1, EB12, MyD116, MacMARCKS, MIP-1b, MIP-1a, PEP, CD72 are increased as a result of the introduction of the drug candidate.

The invention further provides methods of screening for a bioactive agent capable of binding to a B lymphocyte modulator protein (BLMP). The BLMP and a candidate bioactive agent are combined. The binding of the candidate agent to the BLMP is then determined. In some such methods, the BLMP is selected from the group consisting of Egr-1, Egr-2, Nur77, c-myc, MIP-1a, MIP-1b,BL34, gfi-1, NAB2, neurogranin, SLAP, A1, E2-20K, SATB1, Cctq, kappa V, pcp-4, TGIF, CD83, ApoE, Aeg-2, CD72, cyclin D2, 1ck, MEF-2C, bmk, IgD, Evi-2, vimentin, CD36, c-fes, c-fos, TRAP, hIP30, Ly6E.1, LRG-21, Fos B, gadd153, mafK, Ah-R, C/EBP beta, EZF, TIS7, TIS11, TIS11b, LSIRF, MKP1, PAC-1, PEP, MacMARCKS, SNK, Stra13, kir/gem, EB12, IL1-R2, MyD116, RP105, uPAR, 4F2, hRab30, Id3, BKLF, LKLF, EFP, bcl-3, caspase 2, GILZ, hIFI-204, hRhoH, TRAF5, LT-beta, IFNg-RII, gadd45, CDC47, NAG, scd2, kappa 0 ig, iap38, G7e, B29, and SCD2.

The invention further provides methods for screening for a bioactive agent capable of modulating the activity of a B lymphocyte modulator protein (BLMP). The BLMP and a candidate bioactive agent are combined. The effect of the candidate agent on the bioactivity of the BLMP is then determined.

In some such methods the BLMP is selected from the group consisting of Egr-1, Egr-2, Nur77, c-myc, MIP-1a, MIP-1b,BL34, gfi-1, NAB2, neurogranin, SLAP, A1, E2-20K, SATB1, Cctq, kappa V, pcp-4, TGIF, CD83, ApoE, Aeg-2, CD72, cyclin D2, 1ck, MEF-2C, bmk, IgD, Evi-2, vimentin, CD36, c-fes, c-fos, TRAP, hIP30, Ly6E.1, LRG-21, Fos B, gadd153, mafK, Ah-R, C/EBP beta, EZF, TIS7, TIS11, TIS11b, LSIRF, MKP1, PAC-1, PEP, MacMARCKS, SNK, Stra13, kir/gem, EB12, IL1-R2, MyD116, RP105, uPAR, 4F2, hRab30, Id3, BKLF, LKLF, EFP, bcl-3, caspase 2, GILZ, hIFI-204, hRhoH, TRAF5, LT-beta, IFNg-RII, gadd45, CDC47, NAG, scd2, kappa 0 ig, iap38, G7e, B29, and SCD2.

The invention further provides a method of evaluating the effect of an immunosuppressive drug. In such methods, the drug is administered to a patient; b) a cell sample is removed from the patient; and c) the expression profile of the cell sample is determined. Some such methods further comprise comparing the expression profile to an expression profile of a healthy individual. In some such methods the expression profile includes at least one gene selected from the group consisting of Egr-1, Egr-2, Nur77, c-myc, MIP-1a, MIP-1b, BL34, gfi-1, NAB2, neurogranin, SLAP, A1, E2-20K, SATB1, Cctq, kappa V, pcp-4, TGIF, CD83, ApoE, Aeg-2, CD72, cyclin D2, 1ck, MEF-2C, bmk, IgD, Evi-2, vimentin, CD36, c-fes, c-fos, TRAP, hIP30, Ly6E.1, LRG-21, Fos B, gadd153, mafk, Ah-R, C/EBP beta, EZF, TIS7, TIS11, TIS11b, LSIRF, MKP1, PAC-1, PEP, MacMARCKS, SNK, Stra13, kir/gem, EB12, IL1-R2, MyD116, RP105, uPAR, 4F2, hRab30, Id3, BKLF, LKLF, EFP, bcl-3, caspase 2, GILZ, hIFI-204, hRhoH, TRAF5, LT-beta, IFNg-RII, gadd45, CDC47, NAG, scd2, kappa 0 ig, iap38, G7e, B29, and SCD2.

The invention further provides an array of probes. The array comprises a support bearing a plurality of nucleic acid probes complementary to a plurality of mRNAs fewer than 1000 in number, wherein the plurality of mRNA probes includes an mRNA expressed by a gene selected from the group consisting of Egr-1, Egr-2, Nur77, c-myc, MIP-1a, MIP-1b,BL34, gfi-1, NAB2, neurogranin, SLAP, A1, E2-20K, SATB1, Cctq, kappa V, pcp-4, TGIF, CD83, ApoE, Aeg-2, CD72, cyclin D2, 1ck, MEF-2C, bmk, IgD, Evi-2, vimentin, CD36, c-fes, c-fos, TRAP, hIP30, Ly6E.1, LRG-21, Fos B, gadd153, mafK, Ah-R, C/EBP beta, EZF, TIS7, TIS11, TIS11b, LSIRF, MKP1, PAC-1, PEP, MacMARCKS, SNK, Stra13, kir/gem, EB12, IL1-R2, MyD116, RP105, uPAR, 4F2, hRab30, Id3, BKLF, LKLF, EFP, bcl-3, caspase 2, GILZ, hIFI-204, hRhoH, TRAF5, LT-beta, IFNg-RII, gadd45, CDC47, NAG, scd2, kappa 0 ig, iap38, G7e, B29, and SCD2. Some such arrays comprise a plurality of sets of probes wherein each set of probes iscomplementary to subsequences from a mRNA. In some arrays the probes are cDNA sequences.

BRIEF DESCRIPTION OF THE DRAWINGS

FIGS. 1A–1D: Gene expression changes in B lymphocytes responding to foreign antigen. FIG. 1A. Genes with increased mRNA levels after 1 hr stimulation. 37 genes that showed significantly ($p<0.00018$) increased expression (see methods) and showed a median fold change of >1.75 were sorted by putative function. (CD72 is also shown but only increased 1.5 fold. BL34 is represented twice on the arrays, both sets of data are shown.) Each line represents one experiment. The left end of the line shows hybridization intensity in resting B cells mock stimulated in medium alone for one hour, the right end of the line shows intensity in B cells stimulated for one hour through the antigen receptor. Of the seven experiments shown, 3 experiments were with $Ig^{HEL}$ transgenic B cells stimulated with medium alone or with HEL, and 4 experiments were with non-transgenic B cells stimulated with medium alone or with anti-mu. Analysis of variance showed that the basal profiles and responses to stimulation for $Ig^{HEL}$ and non-transgenic B cells were essentially identical and the results have been presented together for clarity. Spiking known concentrations of bacterial transcripts allows an approximate calibration of 5 intensity units/copy/cell assuming 300, 000 transcripts per cell. FIG. 1B. Genes with decreased mRNA levels after 1 hr stimulation. Hybridization intensities are represented as for FIG. 1A. (GILZ is represented twice on the arrays, both sets of data are shown.). FIG. 1C. 1 and 6 hr timepoints of transcripts increased at 1 hr. Results are from 2 experiments showing HEL stimulation of $Ig^{HEL}$ transgenic B cells. Each experiment is represented by a line. The left end of the line is the intensity of the transcript in B cells mock stimulated for 1 hr, the middle of the line is the intensity after 1 hr stimulation with HEL, the end of the line is the intensity after 6 hr stimulation with HEL. Genes are shown in order of exaggerated, sustained and transient increases relative to mock and 1 hr stimulated samples. FIG. 1D. 1 and 6 hr timepoints of transcripts decreased at 1 hr. Results are from 2 experiments with HEL stimulation of Ig transgenic B cells and are represented as in FIG. 1C.

FIG. 2A. Genes upregulated in tolerant cells compared to naïve cells. The left end of each line represents hybridization level in naïve $Ig^{HEL}$ cells, the right end of the line represents hybridization level in tolerant sHEL/$Ig^{HEL}$ cells. Data points that are joined are from separate cell populations from genetically distinct animals—each line represents samples prepared in parallel on the same day. Five sets of data were derived from negatively depleted B cell preparations and two sets from FACS-sorted cells. One set of preparations included two tolerant cell samples and one naïve cell sample. This set is represented as 2 lines joining the naïve cell hybridization intensity to each of the tolerant cell intensities. FIG. 2B. Genes downregulated in tolerant cells compared to naïve cells. Data is represented as in FIG. 2A.

FIGS. 3A–3D. Gene expression changes in B lymphocytes responding to foreign antigen in the presence of FK506 or PD98059. FIG. 3A. FK506 sensitivity of the 1 hr upregulated genes defined in FIG. 1. B cells were stimulated in the presence or absence of FK506, or were mock stimulated. Data are shown from 5 experiments and genes are shown in increasing order of median FK506 sensitivity. Each line represents one experiment. The left end of the line is hybridization intensity in resting B cells, the middle of the line is intensity in B cells stimulated for one hour through the antigen receptor and the right end of the line is intensity in B cells stimulated for one hour in the presence of FK506. Of the five experiments shown, 3 experiments were with IgHEL transgenic B cells stimulated with medium, HEL or HEL/FK506, and 2 experiments were with non-transgenic B cells stimulated with medium, anti-mu or anti-mu/FK506. FIG. 3B. FK506 sensitivity of the 1 hr down-regulated genes. Data is represented as for FIG. 3A. FIG. 3C. Correlation between sensitivity to FK506 and sensitivity to EGTA for antigen-induced transcripts. For the 37 induced genes defined in FIG. 1A, the relative induction in the presence of EGTA was calculated as average (antigen/EGTA-mock)/(antigen-mock), in two experiments with IgHEL transgenic cells stimulated with HEL. For the same transcripts, relative induction in the presence of FK506 was calculated as median of(antigen FK506-mock)/(antigen-mock) over 5 experiments. FIG. 3D. Upper two panels: upregulation of Egr-1 by anti-mu stimulation of non-transgenic B cells is inhibited by PD98059 with an IC50 of ~5 $\mu$M. Regulation of other 1 hour response genes is less sensitive to PD98059. Lower panel: 3 transcripts upregulated by both foreign and self antigen are sensitive to PD98059. Left most four columns for each gene represent data from non-transgenic B cells stimulated with anti-mu, right most 3 columns represent data from $Ig^{HEL}$ transgenic B cells stimulated with HEL.

FIG. 4A. Summary table of biochemical pathways in tolerant cells and naïve cells exposed to foreign antigen in the presence or absence of FK506 and PD98059. FIG. 4B. Potential mechanisms of tolerance, immunity and immunosuppression suggested by the gene expression analysis. Font size reflects mRNA or protein expression level relative to mock stimulated cells (immunosuppression and activation panels) or naïve cells (tolerance panel). Tolerant cells have decreased surface IgM (sIgM) but increased IgD (mRNA and protein): sIg engagement by self-antigen causes decreased tyrosine phosphorylation relative to activated cells. Proximal signaling from sIg can be modulated in activated and tolerant cells by recruitment of SHP1 by increased CD72. Activation of naïve cells causes a robust calcium flux that triggers NfkB, JNK and NFAT. All these pathways are blocked by FK506 through inhibition of calcineurin: calmodulin action can be regulated in naïve and immunosuppressed cells by neurogranin and in tolerant cells by neurogranin and pcp-4. Egr family transcription is predicted to be different under the 3 conditions: in activated cells both Egr-1 and Egr-2 are upregulated preceding upregulation of NAB2; in immunosuppressed cells, only Egr-1 is upregulated; and in tolerant cells Egr-1 and Egr-2 are only weakly upregulated and can have different effects on transcription in the presence of increased NAB2. The balance between mitosis and apoptosis is likely to be in part determined by upregulation of the proto-oncogenes c-myc and LSIRF and the anti-apoptotic gene A1 in activated cells. These changes are blocked by tolerance and partially blocked by FK506. Downregulation of LKLF, which is sufficient to cause T cell activation, is partially inhibited by FK506 and is blocked in tolerance. Upregulation of surface activation markers CD69 and B7.2 is uninhibited by FK506 but is blocked in tolerance. The level of B7.2 on B cells is critical in interaction with antigen specific T cells.

DETAILED DESCRIPTION

1. Definitions

Figure 2A:
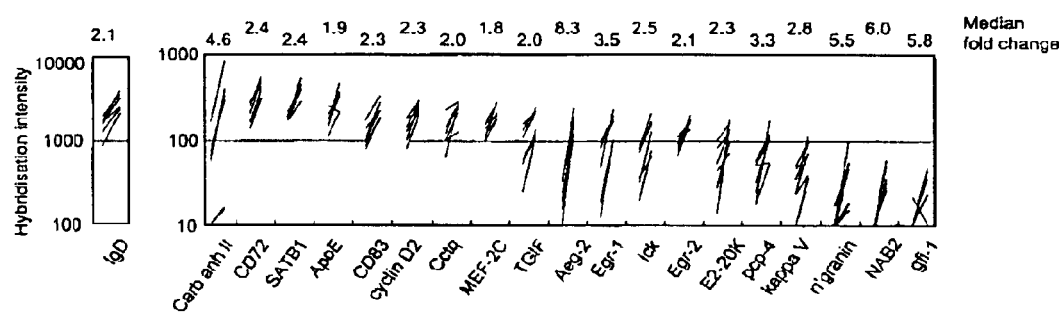
FIGS. 2A and 2B. Gene expression changes in B lymphocytes responding to self antigen.

The term patient includes mammals, such as humans, domestic animals (e.g., dogs or cats), farm animals (cattle, horses, or pigs), monkeys, rabbits, rats, mice, and other laboratory animals.

The terms "nucleic acid" or "nucleic acid molecule" refer to a deoxyribonucleotide or ribonucleotide polymer in either single- or double-stranded form, and unless otherwise limited, can encompass known analogs of natural nucleotides that can fimction in a similar manner as naturally occurring nucleotides.

A polynucleotide probe is a single stranded nucleic acid capable of binding to a target nucleic acid of complementary sequence through one or more types of chemical bonds, usually through complementary base pairing, usually through hydrogen bond formation. A polynucleotide probe can include natural (i.e., A, G, C, or T) or modified bases (e.g., 7-deazaguanosine, inosine). Therefore, polynucleotide probes can 5–10,000, 10–5,000, 10–500, 10–50, 10–25, 10–20, 15–25, and 15–20 bases long. Probe are typically about 10–50 bases long, and are often 15–20 bases. In its simplest embodiment, the array includes test probes (also referred to as polynucleotide probes) more than 5 bases long, preferably more than 10 bases long, and some more than 40 bases long. The probes can also be less than 50 bases long. In some cases, these polynucleotide probes can range from about 5 to about 45 or 5 to about 50 nucleotides long, or from about 10 to about 40 nucleotides long, or from about 15 to about 40 nucleotides in length. The probes can also be about 20 or 25 nucleotides in length.

In addition, the bases in a polynucleotide probe can be joined by a linkage other than a phosphodiester bond, so long as it does not interfere with hybridization. Thus, polynucleotide probes can be peptide nucleic acids in which the constituent bases are joined by peptide bonds rather than phosphodiester linkages. The length of probes used as components of pools for hybridization to distal segments of a target sequence often increases as the spacing of the segments increased thereby allowing hybridization to be conducted under greater stringency to increase discrimination between matched and mismatched pools of probes.

Relatively short polynucleotide probes can be sufficient to specifically hybridize to and distinguish target sequences. Therefore, the polynucleotide probes can be less than 50 nucleotides in length, generally less than 46 nucleotides, more generally less than 41 nucleotides, most generally less than 36 nucleotides, preferably less than 31 nucleotides, more preferably less than 26 nucleotides, and most preferably less than 21 nucleotides in length. The probes can also be less than 16 nucleotides, less than 13 nucleotides in length, less than 9 nucleotides in length and less than 7 nucleotides in length.

Typically, arrays can have polynucleotides as short as 10 nucleotides or 15 nucleotides. In addition, 20 or 25 nucleotides can be used to specifically detect and quantify nucleic acid expression levels. Where ligation discrimination methods are used, the polynucleotide arrays can contain shorter polynucleotides. Arrays containing longer polynucleotides are also suitable. High density arrays can comprise greater than about 100, 1000, 16,000, 65,000, 250,000 or even greater than about 1,000,000 different polynucleotide probes.

The term "target nucleic acid" refers to a nucleic acid (often derived from a biological sample), to which the polynucleotide probe is designed to specifically hybridize. It is either the presence or absence of the target nucleic acid that is to be detected, or the amount of the target nucleic acid that is to be quantified. The target nucleic acid has a sequence that is complementary to the nucleic acid sequence of the corresponding probe directed to the target. The term target nucleic acid can refer to the specific subsequence of a larger nucleic acid to which the probe is directed or to the overall sequence (e.g., gene or mRNA) whose expression level it is desired to detect. The difference in usage can be apparent from context.

"Subsequence" refers to a sequence of nucleic acids that comprise a part of a longer sequence of nucleic acids.

"Gene" refers to a unit of inheritable genetic material found in a chromosome, such as in a human chromosome. Each gene is composed of a linear chain of deoxyribonucleotides which can be referred to by the sequence of nucleotides forming the chain. Thus, "sequence" is used to indicate both the ordered listing of the nucleotides which form the chain, and the chain which has that sequence of nucleotides. The term "sequence" is used in the same way in referring to RNA chains, linear chains made of ribonucleotides. The gene includes regulatory and control sequences, sequences which can be transcribed into an RNA molecule, and can contain sequences with unknown function. Some of the RNA products (products of transcription from DNA) are messenger RNAs (mRNAs) which initially include ribonucleotide sequences (or sequence) which are translated into a polypeptide and ribonucleotide sequences which are not translated. The sequences which are not translated include control sequences, introns and sequences with unknowns function. It can be recognized that small differences in nucleotide sequence for the same gene can exist between different persons, or between normal cells and cancerous cells, without altering the identity of the gene.

"Gene expression pattern" means the set of genes of a specific tissue or cell type that are transcribed or "expressed" to form RNA molecules. Which genes are expressed in a specific cell line or tissue can depend on factors such as tissue or cell type, stage of development or the cell, tissue, or target organism and whether the cells are normal or transformed cells, such as cancerous cells. For example, a gene can be expressed at the embryonic or fetal stage in the development of a specific target organism and then become non-expressed as the target organism matures. Alternatively, a gene can be expressed in liver tissue but not in brain tissue of an adult human.

Specific hybridization refers to the binding, duplexing, or hybridizing of a molecule only to a particular nucleotide sequence under stringent conditions when that sequence is present in a complex mixture (e.g., total cellular) DNA or RNA. Stringent conditions are conditions under which a probe can hybridize to its target subsequence, but to no other sequences. Stringent conditions are sequence-dependent and are different in different circumstances. Longer sequences hybridize specifically at higher temperatures. Generally, stringent conditions are selected to be about 5° C. lower than the thermal melting point ($T_m$) for the specific sequence at a defined ionic strength and pH. The $T_m$ is the temperature (under defined ionic strength, pH, and nucleic acid concentration) at which 50% of the probes complementary to the target sequence hybridize to the target sequence at equilibrium. (As the target sequences are generally present in excess, at $T_m$, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes (e.g., 10 to 50 nucleotides). Stringent conditions can also be achieved with the addition of destabilizing agents such as formamide or tetraalkyl ammonium salts. For example, conditions of 5×SSPE (750 mM NaCl, 50 mM Na Phosphate, 5 mM EDTA, pH 7.4) and a temperature of 25–30° C. are suitable for allele-specific probe hybridizations. (See Sambrook et al., *Molecular Cloning* 1989).

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351–360 (1987). The method used is similar to the method described by Higgins & Sharp, *CABIOS* 5:151–153 (1989). Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387–395 (1984).

Another example of algorithms that are suitable for determining percent sequence identity and sequence similarity are the BLAST and the BLAST 2.0 algorithm, which are described in Altschul et al., *J. Mol. Biol.* 215:403–410 (1990) and Altschul et al., *Nucleic Acids Res.* 25:3389–3402 (1977)). Software for performing BLAST analyses is publicly available through the National Center for Biotechnology Information. The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSLUM62 scoring matrix (see Henikoff & Henikoff, *Proc. Natl. Acad. Sci. USA* 89:10915 (1989)).

The term antibody is used to include intact antibodies and binding fragments thereof. Typically, fragments compete with the intact antibody from which they were derived and with other antibodies for specific binding to an antigen. The term antibody includes polyclonal antibodies, monoclonal antibodies, chimeric antibodies and humanized antibodies, produced by immunization, from hybridomas, or recombinantly.

The term molecule is used broadly to mean an organic or inorganic chemical such as a drug; a peptide, including a variant or modified peptide or peptide-like substance such as a peptidomimetic or peptoid; or a protein such as an antibody or a growth factor receptor or a fragment thereof, such as an $F_v$, $F_c$ or $F_{ab}$ fragment of an antibody, which contains a binding domain. A molecule can be nonnaturally occurring, produced as a result of in vitro methods, or can be naturally occurring, such as a protein or fragment thereof expressed from a cDNA library.

The term specific binding (and equivalent phrases) refers to the ability of a binding moiety (e.g., a receptor, antibody, ligand or antiligand) to bind preferentially to a particular target molecule (e.g., ligand or antigen) in the presence of a heterogeneous population of proteins and other biologics (i.e., without significant binding to other components present in a test sample). Typically, specific binding between two entities, such as a ligand and a receptor, means a binding affinity of at least about $10^6$ M$^{-1}$, and preferably at least about $10^7$, $10^8$, $10^9$, or $10^{10}$ M$^{-1}$. In some embodiments specific (or selective) binding is assayed (and specific binding molecules identified) according to the method of U.S. Pat. No. 5,622,699; this reference and all references cited therein are incorporated herein by reference. Typically a specific or selective reaction according to this assay is at least about twice background signal or noise and more typically at least about 5 or at least about 100 times background, or more.

When the binding moiety is an antibody, a variety of immunoassay formats can be used to select antibodies that are specifically immunoreactive with a particular protein. For example, solid-phase ELISA immunoassays are routinely used to select monoclonal antibodies specifically immunoreactive with an antigen. See Harlow and Lane (1988) *Antibodies, A Laboratory Manual*, Cold Spring Harbor Publications, New York, for a description of immunoassay formats and conditions that can be used to determine specific immunoreactivity (this reference and references cited therein are incorporated herein by reference).

The term "autoimmune disease" refers to a spontaneous or induced malfunction of the immune system of mammals in which the immune system fails to distinguish between foreign immunogenic substances within the mammal and/or autologous ("self") substances and, as a result, treats autologous ("self") tissues and substances as if they were foreign and mounts an immune response against them. Autoimmune disease is characterized by production of either antibodies that react with self tissue, and/or the activation of immune effector T cells that are autoreactive to endogenous self antigens. Three main immunopathologic mechanisms act to mediate autoimmune diseases: 1) autoantibodies are directed against functional cellular receptors or other cell surface molecules, and either stimulate or inhibit specialized cellular function with or without destruction of cells or tissues; 2) autoantigen—autoantibody immune complexes form in intercellular fluids or in the general circulation and ultimately mediate tissue damage; and 3) lymphocytes produce tissue lesions by release of cytokines or by attracting other destructive inflammatory cell types to the lesions. These inflammatory cells in turn lead to production of lipid mediators and cytokines with associated inflammatory disease.

The term "inflammation" refers to both acute responses (i.e., responses in which the inflammatory processes are active) and chronic responses (i.e., responses marked by slow progression and formation of new connective tissue). Acute and chronic inflammation may be distinguished by the cell types involved. Acute inflammation often involves polymorphonuclear neutrophils; whereas chronic inflammation is normally characterized by a lymphohistiocytic and/or granulomatous response. Inflammation includes reactions of both the specific and non-specific defense systems. A specific defense system reaction is a specific immune system reaction response to an antigen (possibly including an autoantigen). A non-specific defense system reaction is an inflammatory response mediated by leukocytes incapable of immunological memory. Such cells include granulocytes, macrophages, neutrophils and eosinophils. Examples of specific types of inflammation are diffuse inflammation, focal inflammation, croupous inflammation, interstitial inflammation, obliterative inflammation, parenchymatous inflammation, reactive inflammation, specific inflammation, toxic inflammation and traumatic inflammation.

The term "immune-mediated" refers to a process that is either autoimmune or inflammatory in nature.

The term "perfect match probe" refers to a probe that has a sequence that is perfectly complementary to a particular target sequence. The test probe is typically perfectly complementary to a portion (subsequence) of the target sequence. The perfect match (PM) probe can be a "test probe," a "normalization control" probe, an expression level control probe and the like. A perfect match control or perfect match probe is, however, distinguished from a "mismatch control" or "mismatch probe."

The term "mismatch control" or "mismatch probe" refer to probes whose sequence is deliberately selected not to be perfectly complementary to a particular target sequence. For each mismatch (MM) control in a high-density array there typically exists a corresponding perfect match (PM) probe that is perfectly complementary to the same particular target sequence. The mismatch can comprise one or more bases. While the mismatch(es) can be located anywhere in the mismatch probe, terminal mismatches are less desirable as terminal mismatch is less likely to prevent hybridization of the target sequence.

The term "probe set" comprises at least a plurality of genes perfectly matched with a known target sequence.

The terms "background" or "background signal intensity" refer to hybridization signals resulting from non-specific binding, or other interactions, between the labeled target nucleic acids and components of the polynucleotide array (e.g., the polynucleotide probes, control probes, or the array substrate). Background signals can also be produced by intrinsic fluorescence of the array components themselves. A single background signal can be calculated for the entire array, or a different background signal can be calculated for each region of the array. In some embodiments, background is calculated as the average hybridization signal intensity for the lowest 1% to 10% of the probes in the array, or region of the array. In expression monitoring arrays (i.e., where probes are preselected to hybridize to specific nucleic acids (genes), a different background signal can be calculated for each target nucleic acid. Where a different background signal is calculated for each target gene, the background signal is calculated for the lowest 1% to 10% of the probes for each gene. Where the probes to a particular gene hybridize well and thus appear to be specifically binding to a target sequence, they should not be used in a background signal calculation. Alternatively, background can be calculated as the average hybridization signal intensity produced by hybridization to probes that are not complementary to any sequence found in the sample (e.g., probes directed to nucleic acids of the opposite sense or to genes not found in the sample such as bacterial genes where the sample is of mammalian origin). Background can also be calculated as the average signal intensity produced by regions of the array that lack any probes at all.

The term "quantifying" when used in the context of quantifying nucleic acid abundance or concentrations (e.g., transcription levels of a gene) can refer to absolute or to relative quantification. Absolute quantification can be accomplished by inclusion of known concentration(s) of one or more target nucleic acids (e.g., control nucleic acids such as BioB or with known amounts the target nucleic acids themselves) and referencing the hybridization intensity of unknowns with the known target nucleic acids (e.g., through generation of a standard curve). Alternatively, relative quantification can be accomplished by comparison of hybridization signals between two or more genes, or between two or more treatments to quantify the changes in hybridization intensity and, by implication, transcription level.

The term "cluster" or "clustering" refers to clustering algorithms, such as principal components analysis and variable clustering analysis. These algorithms serve to "cluster" cells into groups. The purpose of clustering is to place the isolates into groups or clusters suggested by the data, not defined a priori, such that isolates in a given cluster tend to be similar and isolates in different clusters tend to be dissimilar. Methods of clustering are described in Tamayo et al., *Proc. Natl. Acad. Sci U.S.A.* (1999) 96: 2907–2912.

2. Gene Expression Profiles

The present invention provides novel methods for screening for compositions which modulate B cell activity. The expression levels of genes are determined for different cellular states of B cells to provide expression profiles. A B cell expression profile of a particular B cell state can be a "fingerprint" of the state; while two states can have any particular gene similarly expressed, the evaluation of a number of genes simultaneously allows the generation of a gene expression profile that is unique to the state of the cell. By comparing expression profiles of B cells in naive, activated, immunosuppressed, tolerant or resting states, information regarding which genes are important (including both up- and down-regulation of genes) in each of these states is obtained. This information can then be used in a number of ways. For example, the evaluation of a particular treatment regime can be evaluated: does an immunosuppressive drug act like an immunosuppressive drug in this particular patient. Similarly, diagnosis can be done or confirmed: does this patient have the gene expression profile of immunosuppressed B cells. Furthermore, these gene expression profiles can be used in drug candidate screening to find drugs that mimic a particular expression profile; for example, screening can be done for drugs that induce B cell tolerance as evidenced by a tolerant expression profile. Accordingly, genes are identified and described which are differentially expressed within and among B cells in different states, from which the expression profiles are generated as further described herein. For example, determinations of differentially expressed nucleic acids are provided herein for B cells which are resting, activated, immunosuppressed, naive, and tolerant.

"Differential expression," or grammatical equivalents as used herein, refers to both qualitative as well as quantitative differences in the genes' temporal and/or cellular expression patterns within and among B cells. Thus, a differentially expressed gene can qualitatively have its expression altered, including an activation or inactivation in, for example, tolerant versus immunosuppressed cells, rested, naive or activated cells, or in a healthy B cell response versus an abnormal B cell response. Genes can be turned on or turned off in a particular state, relative to another state. Any comparison of two or more states can be made. Such a qualitatively regulated gene will exhibit an expression pattern within a state or cell type which can be detectable by standard techniques in one such state or cell type, but can be not detectable in both. Alternatively, the determination can be quantitative in that expression is increased or decreased; that is, the expression of the gene is either upregulated, resulting in an increased amount of transcript, or downregulated, resulting in a decreased amount of transcript. The degree to which expression differs need only be large enough to quantify using standard characterization techniques, for example, by using Affymetrix GeneChip™ expression arrays (Lockhart, *Nature Biotechnology*, (1996) 14:1675–1680; this reference and all references cited therein are incorporated by reference). Other methods include, but are not limited to, quantitative reverse transcriptase PCR, Northern analysis and RNase protection. Preferably the change or modulation in expression (i.e., upregulation or downregulation) is at least about 5%, more preferably at least about 10%, more preferably, at least about 20%, more preferably, at least about 30%, or more preferably by at least about 50%, or at least about 75%, and more preferably at least about 90%.

Any one, two, three, four, five, or ten or more genes can be evaluated. These genes include, but are not limited to, Egr-1, Egr-2, Nur77, c-myc, MIP-1a, MIP-1b, BL34, gfi-1, NAB2, neurogranin, SLAP, A1, E2-20K, SATB1, Cctq, kappa V, pcp-4, TGIF, CD83, ApoE, Aeg-2, CD72, cyclin D2, 1ck, MEF-2C, bmk, IgD, Evi-2, vimentin, CD36, c-fes, c-fos, TRAP, hIP30, Ly6E.1, LRG-21, Fos B, gadd153, mafk, Ah-R, C/EBP beta, EZF, TIS7, TIS11, TIS11b, LSIRF, MKP1, PAC-1, PEP, MacMARCKS, SNK, Stra13, kir/gem, EB12, IL1-R2, MyD116, RP105, uPAR, 4F2, hRab30, Id3, BKLF, LKLF, EFP, bcl-3, caspase 2, GILZ, hIFI-204, hRhoH, TRAF5, LT-beta, IFNg-RII, gadd45, CDC47, NAG, scd2, kappa 0 ig, iap38, G7e, B29, and SCD2 (the accession numbers for these genes can be found in Table 1). Generally, oligonucleotide sequences used in the evaluation of these genes are derived from their 3' untranslated regions.

Differentially expressed genes can represent "expression profile genes", which includes "target genes". "Expression profile gene," as used herein, refers to a differentially expressed gene whose expression pattern can be used in methods for identifying compounds useful in the modulation of B cell states or activity, or the treatment of disorders, or alternatively, the gene can be used as part of a prognostic or diagnostic evaluation of immune disorders. For example, the effect of the compound on the expression profile gene normnally displayed in connection with a particular state, such as tolerance, for example, can be used to evaluate the efficacy of the compound to modulate that state, or preferably, to induce or maintain that state. Such assays are further described below. Alternatively, the gene can be used as a diagnostic or in the treatment of immune disorders as also further described below. In some instances, only a fragment of an expression profile gene is used, as further described below.

"Expression profile," as used herein, refers to the pattern of gene expression generated from two up to all of the expression profile genes which exist for a given state. As outlined above, an expression profile is in a sense a "fingerprint" or "blueprint" of a particular cellular state; while two or more states have genes that are similarly expressed, the total expression profile of the state will be unique to that state. The gene expression profile obtained for a given B cell state can be useful for a variety of applications, including diagnosis of a particular disease or condition and evaluation of various treatment regimes. In addition, comparisons between the expression profiles of different B cell states can be similarly informative. An expression profile can include genes which do not appreciably change between two states, so long as at least two genes which are differentially expressed are represented. The gene expression profile can also include at least one target gene, as defined below. Alternatively, the profile can include all of the genes which represent one or more states. Specific expression profiles are described below.

Gene expression profiles can be defined in several ways. For example, a gene expression profile can be the relative transcript level of any number of particular set of genes. Alternatively, a gene expression profile can be defined by comparing the level of expression of a variety of genes in one state to the level of expression of the same genes in another state. For example, genes can be either upregulated, downregulated, or remain substantially at the same level in both states.

The expression profile for an activated B cell compared to a naïve resting B cell following lymphocyte activation for one hour is shown in FIG. 1. Lymphocyte activation as used herein refers to the antigen induced progression of B cells from the G0 phase to the G2 phase of the cell cycle. FIG. 1A shows the following upregulated genes after lymphocyte activation for 1 hour: Egr-1, Egr-2, NAB2, mafk, LRG-21, Fos B. cfos, c-myc, Stra13, AhR, gadd153, C/EBP beta, TIS11, TIS11b, gfi-1, EZF, Nur77, LSIRF, SNK, PAC-1, kir/gem, MacMARCKS, PEP, MKP1, hRab30, MIP-1a, MIP-1b, EBI2, BL34, ILI-R2, TIS7, MyD116, A1, uPAR, RP105, Evi-2, 4F2 and CD72; these genes are referred to herein as upregulated early activation B cell expression profile genes. FIG. 1B shows the following genes that are downregulated after lymphocyte activation for one hour: Id3, BKLF, LKLF, EFP, Stat1, bcl-3, hRhoH, TRAF5, SLAP, LT-beta, IFNg-RII, GILZ, Caspase 2, gadd45, mCDC47, NAG, scd2, kappa 0 Ig, B29, iap38, G7e, and hIFI-204; these genes are referred to herein as downregulated early activation B cell expression profile genes.

Figure 2B:
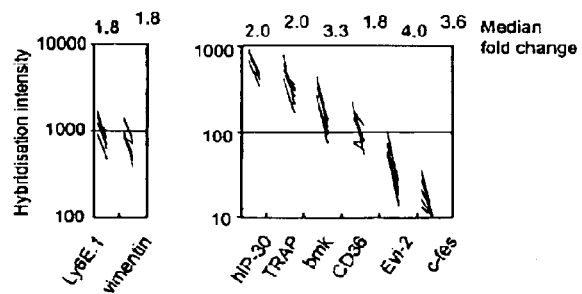

Also provided herein are gene expression profiles for tolerant B cells compared to naïve B cells after activation by self or foreign antigen. Tolerance is generally defined as a state of altered responsiveness to a particular antigen that prevents development of either a cellular- or antibody-based immune response to that antigen. FIG. 2A shows genes that are upregulated in tolerant cells compared to naïve cells after activation by self-antigen: IgD, carb anh II, CD72, SATB1, ApoE, CD83, cyclin D2, Cctq, MEF-2C, TGIF, Aeg-2, Egr-1, 1ck, Egr-2, E2-20K, pcp-4, kappa V, neurogranin, NAB2 and gfi-1. FIG. 2B shows the following genes that are downregulated in tolerant cells compared to naïve cells after activation by self-antigen: Ly6E.1, vimentin, hIP-30, TRAP, bmk, CD36, Evi-2, and c-fes.

Figure 3A:
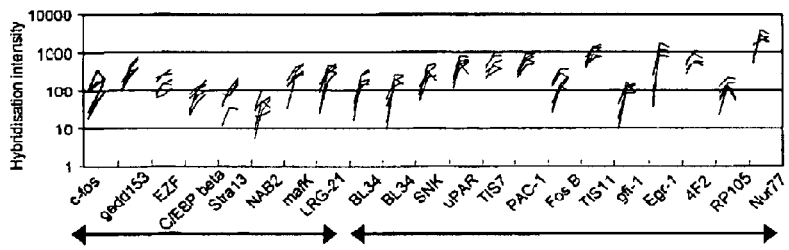
Figure 3B:
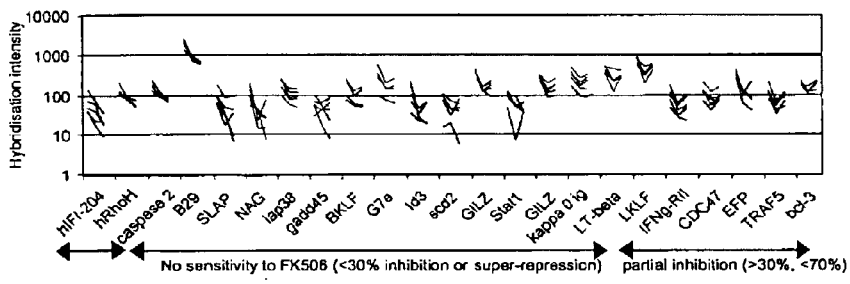
Figure 3C:
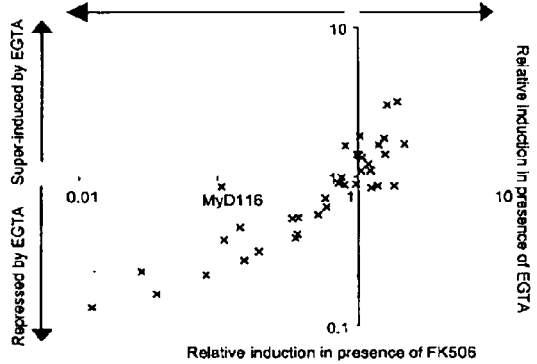

Also provided herein are gene expression profiles for B cell activation inhibited by immunosuppressive agents, as generally outlined below. Examples of immunosuppressive drugs which inhibit B cell activation include FK506 (see, e.g., Wicker, L. S. et al., *Eur J. Immunol* (1990) 20: 2277–83) or cyclosporin A (see, e.g., *Clin Immunol Immunopathol* (1996) 80(3 Pt 2): S40–5). As used herein, immunosuppression and tolerance include the suppression of B lymphocyte activation. Agents which modulate immunosuppression are referred to herein as immunosuppressants, immunosuppressant modulators, or immunosuppressive agents. The expression profile for immunosuppressed B cells compared to activated and resting B cells is shown in FIG. 3. FIG. 3A and FIG. 3B show the upregulated and downregulated early activation B cell expression profile genes where each line individually shows one gene in the resting state, activated state and immunosuppressed state by reading the line left to right respectively. Thus, a gene sensitive to immunosuppression is represented by a peak for upregulated genes (FIG. 3A) and valleys for downregulated genes (see FIG. 3B). FIG. 3A shows the immunosuppressive sensitivity of the following upregulated early activation B cell expression profile genes in order of sensitivity, where the right side of FIG. 3A shows the most sensitive genes. "Sensitive" in this context means that gene expression is downregulated as compared to the active state. Sensitive upregulated early activation B cell expression profile genes include: LSIRF, kir/gem, MKP1, hRab30, AhR, c-myc, IL1-R2, TIS11b, Evi-2, A1, EB12, MyD116, MacMARCKS, MIP-1b, Egr-2, MIP-1a, PEP and CD72. Upregulated early activation B cell expression profile genes that are less than 30% inhibited by immunosuppressive agents include: c-fos, gadd153, EZF, C/EBP beta, Stra13, mafK, LRG-21, BL34, SNK, uPAR, TIS7, PAC-1, Fos B, TIS11, gfi-1, Egr-1, 4F2, RP 105 and Nur77.

FIG. 3B shows the immunosuppressive sensitivity of the downregulated early activation B cell expression profile genes in order of sensitivity, where the right side of FIG. 3B shows the most sensitive genes. Sensitive downregulated early activation B cell expression profile genes include: LKLF, IFNg-RII, CDC47, EFP, TRAF5 and bcl-3. Downregulated early activation B cell expression profile genes that are less than 30% inhibited by immunosuppressive agents include: hIFI-204, hRhoH, caspase 2, B29, SLAP, NAG iap38, gadd45, BKLF, G7e, Id3, scd2, GILZ, Stat1, kappa 0 ig, and LT-beta.

A gene expression profile can include a combination of at least two of Egr-1, Nur77, c-myc, MIP-1a, MIP-1b, BL34, gfi-1, NAB2, neurogranin, and SLAP. A1 can also be included in the expression profile of tolerant cells as shown in FIG. 4. Another target gene for tolerance is B7.2, which upregulation is inhibited in tolerance but not in immunosuppression. A preferred target gene for tolerance or tolerance modulation is NAB2 which is upregulated in tolerant B cells compared to resting or naive cells. Moreover, target genes for tolerance include: CD72, neurogranin, pcp-4, Egr-1, Egr-2, NAB2, myc, LSIRF, A1, and LKLF which are downregulated in tolerance; these changes appear to be unique to the tolerance phenotype and are not seen in response to an activating signal. Agents which modulate or induce a state of tolerance are referred to herein as tolerants. In a preferred expression profile, the total expression profile is recreated by at least one small molecule (e.g., FK506 or cyclosporin A) or other pharmacological intervention. In one embodimnent, at least one of or all of Egr-1, Egr-2, c-myc and c-fos are suppressed while NAB2 is upregulated.

3. Target and Pathway Genes

In addition to expression profile genes, the present invention also provides target genes. "Target gene," as used herein, refers to a differentially expressed expression profile gene whose expression is unique for a particular state, such that the presence or absence of the transcript of a target gene(s) can indicate the state the cell is in. A target gene can be completely unique to a particular state; the presence or absence of the gene is only seen in a particular cell state, or alternatively, cells in all other states express the gene but it is not seen in the first state. Thus for example NAB2 is not expressed in naïve B cells but is expressed in all other states. Alternatively, target genes can be identified as relevant to a comparison of two states, that is, the state is compared to another particular state or standard to determine the uniqueness of the target gene. Target genes can be used in the diagnostic, prognostic, and compound identification methods described herein.

It should be understood that a target gene for a first state can be an expression profile gene for a second state. The presence or absence of a particular target gene in one state can be diagnostic of the state; the same gene in a different state can be an expression profile gene.

Further, pathway genes are provided herein. "Pathway genes" are defined by the ability of their gene products to interact with expression profile genes. Pathway genes can also exhibit target gene and/or expression profile gene characteristics and can be included as modulators of expression profile genes as further described below.

The present invention includes the products of such expression profile, target, and pathway genes, as well as antibodies to such gene products. Furthermore, the engineering and use of cell- and animal-based models of B cell states to which such profiles, genes and gene products can contribute, are also described.

4. Sample Preparation

To measure the transcription level (and thereby the expression level) of a gene or genes, a nucleic acid sample comprising mRNA transcript(s) of the gene or genes, or nucleic acids derived from the mRNA transcript(s) is provided. A nucleic acid derived from an mRNA transcript refers to a nucleic acid for whose synthesis the mRNA transcript or a subsequence thereof has ultimately served as a template. Thus, a cDNA reverse transcribed from an mRNA, an RNA transcribed from that cDNA, a DNA amplified from the cDNA, an RNA transcribed from the amplified DNA, are all derived from the mRNA transcript and detection of such derived products is indicative of the presence and/or abundance of the original transcript in a sample. Thus, suitable samples include mRNA transcripts of the gene or genes, cDNA reverse transcribed from the mRNA, cRNA transcribed from the cDNA, DNA amplified from the genes, RNA transcribed from amplified DNA, and the like.

In some methods, a nucleic acid sample is the total mRNA isolated from a biological sample. The term "biological sample", as used herein, refers to a sample obtained from an organism or from components (e.g., cells) or an organism. The sample can be of any biological tissue or fluid. Frequently the sample is from a patient. Such samples include sputum, blood, blood cells (e.g., white cells), tissue or fine needle biopsy samples, urine, peritoneal fluid, and fleural fluid, or cells therefrom. Biological samples can also include sections of tissues such as frozen sections taken for histological purposes. Often two samples are provided for purposes of comparison. The samples can be, for example, from different cell or tissue types, from different species, from different individuals in the same species or from the same original sample subjected to two different treatments (e.g., drug-treated and control).

5. Method (A) Generation of cDNAs

For example, methods of isolation and purification of nucleic acids are described in detail in WO 97/10365, WO 97/27317, Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part 1. Theory and Nucleic Acid Preparation, P. Tijssen, ed. Elsevier, N.Y. (1993)).

The total nucleic acid can be isolated from a given sample using, for example, an acid quanidinium-phenol-choloroform extraction method and poly $A^+$ mRNA is isolated by oligo dT column chromatography or by using (dT)n magnetic beads (see, e.g., Sambrook et al., Molecular Cloning: A Laboratory Manual ($2^{nd}$ ed.), Vols 1–3, Cold Spring Harbor Laboratory, (1989), or Current Protocols in Molecular Biology, F. Ausubel et al., ed., Breene Publishing and Wiley-Interscience, N.Y. (1987)).

The sample mRNA can be reverse transcribed with a reverse transcriptase and a primer consisting of oligo dT and a sequence encoding the phage T7 promoter to provide single stranded DNA template. The second DNA strand is polymerized using a DNA polymerase. Methods of in vitro polymerization are well known (see, e.g., Sambrook, supra) and this particular method is described in detail by Van Gelder, et al., *Proc. Natl. Acad. Sci. U.S.A* 87: 1663–1667 (1990) report that in vitro amplification according to this method preserves the relative frequencies of the various RNA transcripts. Eberwine et al., *Proc. Natl. Acad. Sci. U.S.A* 89:3010–3014 provide a further protocol that uses two round of amplification via in vitro transcription thereby permitting expression monitoring. Eberwine et al describe another method of amplification in *Methods* (1996) 10(3): 283–8. Another method of amplification is described in Dixon et al., *Nucleic Acids Res* (1998) 26(19): 4426–31. A still further method of amplification is the amplification method described in Dulac et al., Cell (1995) 83: 195–206. An alternative method of amplification is described in U.S. Ser. No. 60/126,796 filed on Mar. 30, 1999, which is herein incorporated by reference.

After amplification, the nucleic acids are typically cleaved into smaller fragments. Cleavage can be achieved by DNaseI digestion, restriction enzyme digestion, or sonication. Nucleic acids are typically labeled. Label can be introduced during amplification either by linkage to one of the primers or by one of the nucleotides being incorporated. Alternatively, labeling can be effected after amplification and cleavage by end-labeling. Detectable labels suitable for use in the present invention include any composition detectable by spectroscopic, photochemical, biochemical, immunochemical, electrical, optical or chemical means; see WO 97/10365.

In general, nucleic acid probes comprising the expression profile genes, including differentially expressed genes and target genes, can be attached to a solid support, generally in an array format, to allow for gene expression monitoring. "Gene" in this context includes full length genes and fragments thereof, and can comprise either the coding strand or its complement, and can be a portion of a gene, a regulatory sequence, genomic DNA, cDNA, RNA including mRNA and rRNA.

In some cases, the differentially expressed nucleic acid can be a fragment, or expressed sequence tag (EST). Once a differentially expressed nucleic acid which is not a full length gene is identified, it can be cloned and, if necessary, its constituent parts recombined to form an entire fall length or mature differentially expressed nucleic acid. Using methods described herein and known in the art, it can be used to identify the full length clone. Wherein the full length nucleic acid has a signal peptide and/or transmembrane region(s), it can be modified to exclude one or more of these regions so as to encode a peptide in its mature soluble form. Once isolated from its natural source, e.g., contained within a plasmid or other vector or excised therefrom as a linear nucleic acid segment, the recombinant differentially expressed nucleic acid can be further-used as a probe to identify and isolate other differentially expressed nucleic acid acids. It can also be used as a "precursor" nucleic acid to make modified or variant differentially expressed nucleic acid acids and proteins. Where two or more nucleic acids overlap, the overlapping portion(s) of one of the overlapping nucleic acids can be omitted and the nucleic acids combined for example by ligation to form a longer linear differentially expressed nucleic acid so as to, for example, encode the full length or mature peptide. The same applies to the amino acid sequences of differentially expressed polypeptides in that they can be combined so as to form one contiguous peptide.

It should be noted that the nucleic acid probes used herein need not be identical to the wild-type genes listed above. Nucleic acids having sequence identity with differentially expressed nucleic acids preferably have about 65% or 75%, more preferably greater than about 80%, even more preferably greater than about 85% and most preferably greater than 90% sequence identity. In some embodiments the sequence identity will be as high as about 93 to 95 or 98%. Sequence identity will be determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biol. 48:443 (1970), by the search for similarity method of Pearson & Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al, Nucl. Acid Res. 12:387–395 (1984), preferably using the default settings, or by inspection.

The PCR method of amplification is described in PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202 (each of which is incorporated by reference for all purposes). Nucleic acids in a target sample are usually labeled in the course of amplification by inclusion of one or more labeled nucleotides in the amplification mix. Labels can also be attached to amplification products after amplification e.g., by end-labeling. The amplification product can be RNA or DNA depending on the enzyme and substrates used in the amplification reaction.

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. U.S.A 86, 1173 (1989)), and self-sustained sequence replication (Guatelli et al., Proc. Nat. Acad. Sci. U.S.A 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

A variety of labels can be incorporated into target nucleic acids in the course of amplification or after amplification. Suitable labels include fluorescein or biotin, the latter being detected by staining with phycoerythrin-streptavidin after hybridization. In some methods, hybridization of target nucleic acids is compared with control nucleic acids. Optionally, such hybridizations can be performed simultaneously using different labels are used for target and control samples. Control and target samples can be diluted, if desired, prior to hybridization to equalize fluorescence intensities.

6. Supports

Supports can be made of a variety of materials, such as glass, silica, plastic, nylon or nitrocellulose. Supports are preferably rigid and have a planar surface. Supports typically have from 1–10,000,000 discrete spatially addressable regions, or cells. Supports having 10–1,000,000 or 100–100,000 or 1000–100,000 cells are common. The density of cells is typically at least 1000, 10,000, 100,000 or 1,000,000 cells within a square centimeter. Typically a single probe per cell. In some supports, all cells are occupied by pooled mixtures of probes. In other supports, some cells are occupied by pooled mixtures of probes, and other cells are occupied, at least to the degree of purity obtainable by synthesis methods, by a single type of polynucleotide. The strategies for probe design described in the present application can be combined with other strategies, such as those described by WO 95/11995, EP 717,113 and WO 97/29212 in the same array.

The location and sequence of each different polynucleotide probe in the array is generally known. Moreover, the large number of different probes can occupy a relatively small area providing a high density array having a probe density of generally greater than about 60, more generally greater than about 100, and most generally greater than about 600, often greater than about 1000, more often greater than about 5,000, most often greater than about 10,000, preferably greater than about 40,000 more preferably greater than about 100,000, and most preferably greater than about 400,000 different polynucleotide probes per cm². The small surface area of the array (often less than about 10 cm², preferably less than about 5 cm² more preferably less than about 2 cm², and most preferably less than about 1.6 cm²) permits the use of small sample volumes and extremely uniform hybridization conditions 7. Synthesis of Probe Arrays Arrays of probes can be synthesized in a step-by-step manner on a support or can be attached in presynthesized form. A preferred method of synthesis is VLSIPS™ (see Fodor et al., 1991, Fodor et al., 1993, Nature 364, 555–556; McGall et al., U.S. Ser. No. 08/445,332; U.S. Pat. No. 5,143,854; EP 476,014), which entails the use of light to direct the synthesis of polynucleotide probes in high-density, miniaturized arrays. Algorithms for design of masks to reduce the number of synthesis cycles are described by Hubbel et al., U.S. Pat. No. 5,571,639 and U.S. Pat. No. 5,593,839. Arrays can also be synthesized in a combinatorial fashion by delivering monomers to cells of a support by mechanically constrained flowpaths. See Winkler et al., EP 624,059. Arrays can also be synthesized by spotting monomers reagents on to a support using an ink jet printer. See id.; Pease et al., EP 728,520.

After hybridization of control and target samples to an array containing one or more probe sets as described above and optional washing to remove unbound and nonspecifically bound probe, the hybridization intensity for the respective samples is determined for each probe in the array. For fluorescent labels, hybridization intensity can be determined by, for example, a scanning confocal microscope in photon counting mode. Appropriate scanning devices are described by e.g., Trulson et al., U.S. Pat. No. 5,578,832; Stem et al., U.S. Pat. No. 5,631,734 and are available from Affymetrix, Inc., under the GeneChip™ label. Some types of label provide a signal that can be amplified by enzymatic methods (see Broude, et al., Proc. Natl. Acad. Sci. U.S.A. 91, 3072–3076 (1994))

8. Design of Arrays (A) Customized and Generic Arrays

The design of arrays for expression monitoring is generally described, for example, WO 97/27317 and WO 97/10365 (these references are herein incorporated by reference). There are two principal categories of arrays. One type of array detects the presence and/or levels of particular mRNA sequences that are known in advance. In these arrays, polynucleotide probes can be selected to hybridize to particular preselected subsequences of mRNA gene sequence. Such expression monitoring arrays can include a plurality of probes for each mRNA to be detected. For analysis of mRNA nucleic acids, the probes are designed to be complementary to the region of the mRNA that is incorporated into the nucleic acids (i.e., the 3' end). The array can also include one or more control probes.

Generic arrays can include all possible nucleotides of a given length; that is, polynucleotides having sequences corresponding to every permutation of a sequence. Thus since the polynucleotide probes of this invention preferably include up to 4 bases (A, G, C, T) or (A, G, C, U) or derivatives of these bases, an array having all possible nucleotides of length X contains substantially $4^X$ different nucleic acids (e.g., 16 different nucleic acids for a 2 mer, 64 different nucleic acids for a 3 mer, 65536 different nucleic acids for an 8 mer). Some small number of sequences can be absent from a pool of all possible nucleotides of a particular length due to synthesis problems, and inadvertent cleavage). An array comprising all possible nucleotides of length X refers to an array having substantially all possible nucleotides of length X. All possible nucleotides of length X includes more than 90%, typically more than 95%, preferably more than 98%, more preferably more than 99%, and most preferably more than 99.9% of the possible number of different nucleotides. Generic arrays are particularly useful for comparative hybridization analysis between two mRNA populations or nucleic acids derived therefrom.

(B) Variations (1) Constant Regions

In both customized and generic array, probes can comprise additional constant regions fused with the variable regions that mediate hybridization to target nucleic acid. In some arrays, constant regions are double stranded thereby providing a site at which hybridized target can ligate to immobilized probes. A constant domain is a nucleotide subsequence that is common to substantially all of the polynucleotide probes. Constant domains are typically located at the terminus of the polynucleotide probe closest to the substrate (i.e., attached to the linker/anchor molecule). The constant regions can comprise virtually any sequence. Some constant regions comprise a sequence or subsequence complementary to the sense or antisense strand of a restriction site (a nucleic acid sequence recognized by a restriction enzyme).

Constant regions can be synthesized de novo on the array or prepared in a separate procedure and then coupled intact to the array. Since the constant domain can be synthesized separately and then the intact constant subsequences coupled to the high density array, the constant domain can be virtually any length. Some constant domains range from 3 nucleotides to about 500 nucleotides in length, more typically from about 3 nucleotides in length to about 100 nucleotides in length, most typically from 3 nucleotides in length to about 50 nucleotides in length. Constant domains can also range from 3 nucleotides to about 45 nucleotides in length, or from 3 nucleotides in length to about 25 nucleotides in length or from 3 to about 15 or even 10 nucleotides in length. Constant domains can also range from about 5 nucleotides to about 15 nucleotides in length.

(2) Control Probes

Either customized or generic probe arrays can contain control probes in addition to the probes described above.

(a) Normalization Controls

Normalization controls are typically perfectly complementary to one or more labeled reference polynucleotides that are added to the nucleic acid sample. The signals obtained from the normalization controls after hybridization provide a control for variations in hybridization conditions, label intensity, reading and analyzing efficiency and other factors that can cause the signal of a perfect hybridization to vary between arrays. Signals (e.g., fluorescence intensity) read from all other probes in the array can be divided by the signal (erg., fluorescence intensity) from the control probes thereby normalizing the measurements.

Virtually any probe can serve as a normalization control. However, hybridization efficiency can vary with base composition and probe length. Normalization probes can be selected to reflect the average length of the other probes present in the array, however, they can also be selected to cover a range of lengths. The normalization control(s) can also be selected to reflect the (average) base composition of the other probes in the array. However one or a fewer normalization probes can be used and they can be selected such that they hybridize well (i.e., no secondary structure) and do not match any target-specific probes.

Normalization probes can be localized at any position in the array or at multiple positions throughout the array to control for spatial variation in hybridization efficiently. The normalization controls can be located at the corners or edges of the array as well as in the middle of the array.

(b) Expression Level Controls

Expression level controls can be probes that hybridize specifically with constitutively expressed genes in the biological sample. Expression level controls can be designed to control for the overall health and metabolic activity of a cell. Examination of the covariance of an expression level control with the expression level of the target nucleic acid can indicate whether measured changes or variations in expression level of a gene is due to changes in transcription rate of that gene or to general variations in health of the cell. Thus, for example, when a cell is in poor health or lacking a critical metabolite the expression levels of both an active target gene and a constitutively expressed gene are expected to decrease. The converse can also be true. Thus where the expression levels of both an expression level control and the target gene appear to both decrease or to both increase, the change can be attributed to changes in the metabolic activity of the cell as a whole, not to differential expression of the target gene in question. Conversely, where the expression levels of the target gene and the expression level control do not covary, the variation in the expression level of the target gene can be attributed to differences in regulation of that gene and not to overall variations in the metabolic activity of the cell.

Virtually any constitutively expressed gene can provide a suitable target for expression level controls. Typically expression level control probes can have sequences complementary to subsequences of constitutively expressed genes including, but not limited to the β-actin gene, the transferrin receptor gene, the GAPDH gene, and the like.

(c) Mismatch Controls

Mismatch controls can also be provided for the probes to the target genes, for expression level controls or for normalization controls. Mismatch controls are typically employed in customized arrays containing probes matched to known mRNA species. For example, some such arrays contain a mismatch probe corresponding to each match probe. The mismatch probe is the same as its corresponding match probe except for at least one position of mismatch. A mismatched base is a base selected so that it is not complementary to the corresponding base in the target sequence to which the probe can otherwise specifically hybridize. One or more mismatches are selected such that under appropriate hybridization conditions (e.g. stringent conditions) the test or control probe can be expected to hybridize with its target sequence, but the mismatch probe cannot hybridize (or can hybridize to a significantly lesser extent). Mismatch probes can contain a central mismatch. Thus, for example, where a probe is a 20 mer, a corresponding mismatch probe can have the identical sequence except for a single base mismatch (e.g., substituting a G, a C or a T for an A) at any of positions 6 through 14 (the central mismatch).

In generic (e.g., random, arbitrary, or haphazard) arrays, since the target nucleic acid(s) are unknown perfect match and mismatch probes cannot be a priori determined, designed, or selected. In this instance, the probes can be provided as pairs where each pair of probes differ in one or more preselected nucleotides. Thus, while it is not known a priori which of the probes in the pair is the perfect match, it is known that when one probe specifically hybridizes to a particular target sequence, the other probe of the pair can act as a mismatch control for that target sequence. The perfect match and mismatch probes need not be provided as pairs, but can be provided as larger collections (e.g., 3, 4, 5, or more) of probes that differ from each other in particular preselected nucleotides.

In both customized and generic arrays mismatch probes can provide a control for non-specific binding or cross-hybridization to a nucleic acid in the sample other than the target to which the probe is complementary. Mismatch probes thus can indicate whether a hybridization is specific or not. For example, if the complementary target is present the perfect match probes can be consistently brighter than the mismatch probes. In addition, if all central mismatches are present, the mismatch probes can be used to detect a mutation. Finally, the difference in intensity between the perfect match and the mismatch probe (I(PM)-I(MM)) can provide a good measure of the concentration of the hybridized material.

(d) Sample Preparation, Amplification, and Quantitation Controls

Arrays can also include sample preparation/amplification control probes. These can be probes that are complementary to subsequences of control genes selected because they do not normally occur in the nucleic acids of the particular biological sample being assayed. Suitable sample preparation/amplification control probes can include, for example, probes to bacterial genes (e.g., Bio B) where the sample in question is a biological sample from a eukaryote.

The RNA sample can then be spiked with a known amount of the nucleic acid to which the sample preparation/amplification control probe is directed before processing. Quantification of the hybridization of the sample preparation/amplification control probe can then provide a measure of alteration in the abundance of the nucleic acids caused by processing steps (e.g., PCR, reverse transcription, or in vitro transcription).

Quantitation controls can be similar. Typically they can be combined with the sample nucleic acid(s) in known amounts prior to hybridization. They are useful to provide a quantitation reference and permit determination of a standard curve for quantifying hybridization amounts (concentrations).

9. Methods of Detection

In one method of detection, mRNA or nucleic acid derived therefrom, typically in denatured form, are applied to an array. The component strands of the nucleic acids hybridize to complementary probes, which are identified by detecting label. Optionally, the hybridization signal of matched probes can be compared with that of corresponding mismatched or other control probes. Binding of mismatched probe serves as a measure of background and can be subtracted from binding of matched probes. A significant difference in binding between a perfectly matched probes and a mismatched probes signifies that the nucleic acid to which the matched probes are complementary is present. Binding to the perfectly matched probes is typically at least 1.2, 1.5, 2, 5 or 10 or 20 times higher than binding to the mismatched probes.

In a variation of the above method, nucleic acids are not labeled but are detected by template-directed extension of a probe hybridized to a nucleic acid strand with the nucleic acid strand serving as a template. The probe is extended with a labeled nucleotide, and the position of the label indicates, which probes in the array have been extended. By performing multiple rounds of extension using different bases bearing different labels, it is possible to determine the identity of additional bases in the tag than are determined through complementarity with the probe to which the tag is hybridized. The use of target-dependent extension of probes is described by U.S. Pat. No. 5,547,839.

In a further variation, probes can be extended with inosine. The inosine strand can be labeled. The addition of degenerate bases, such as inosine (it can pair with all other bases), can increase duplex stability between the polynucleotide probe and the denatured single stranded DNA nucleic acids. The addition of 1–6 inosines onto the end of the probes can increase the signal intensity in both hybridization and ligation reactions on a generic ligation array. This can allow for ligations at higher temperatures. The use of degenerate bases is described in WO 97/27317.

Ligation reactions can offer improved discriminate between fully complementary hybrids and those that differ by one or more base pairs, particularly in cases where the mismatch is near the 5' terminus of the polynucleotide probes. Use of a ligation reaction in signal detection increases the stability of the hybrid duplex, improves hybridization specificity (particularly for shorter polynucleotide probes (e.g., 5 to 12-mers), and optionally, provides additional sequence information. Ligation reactions used in signal detection are described in WO 97/27317. Optionally, ligation reactions can be used in conjunction with template-directed extension of probes, either by inosine or other bases.

10. Analysis of Hybridization Patterns

The position of label is detected for each probe in the array using a reader, such as described by U.S. Pat. No. 5,143,854, WO 90/15070, and Trulson et al., supra. For customized arrays, the hybridization pattern can then be analyzed to determine the presence and/or relative amounts or absolute amounts of known mRNA species in samples being analyzed as described in e.g., WO 97/10365. Comparison of the expression patterns of two samples is useful for identifying mRNAs and their corresponding genes that are differentially expressed between the two samples.

The quantitative monitoring of expression levels for large numbers of genes can prove valuable in elucidating gene function, exploring the causes and mechanisms of disease, and for the discovery of potential therapeutic and diagnostic targets. Expression monitoring can be used to monitor the expression (transcription) levels of nucleic acids whose expression is altered in a disease state. For example, a cancer can be characterized by the overexpression of a particular marker such as the HER2 (c-erbB-2/neu) protooncogene in the case of breast cancer.

Expression monitoring can be used to monitor expression of various genes in response to defined stimuli, such as a drug. This is especially useful in drug research if the end point description is a complex one, not simply asking if one particular gene is overexpressed or underexpressed. Therefore, where a disease state or the mode of action of a drug is not well characterized, the expression monitoring can allow rapid determination of the particularly relevant genes.

In generic arrays, the hybridization pattern is also a measure of the presence and abundance of relative mRNAs in a sample, although it is not immediately known, which probes correspond to which mRNAs in the sample.

However the lack of knowledge regarding the particular genes does not prevent identification of useful therapeutics. For example, if the hybridization pattern on a particular generic array for a healthy cell is known and significantly different from the pattern for a diseased cell, then libraries of compounds can be screened for those that cause the pattern for a diseased cell to become like that for the healthy cell. This provides a detailed measure of the cellular response to a drug.

Generic arrays can also provide a powerful tool for gene discovery and for elucidating mechanisms underlying complex cellular responses to various stimuli. For example, generic arrays can be used for expression fingerprinting. Suppose it is found that the mRNA from a certain cell type displays a distinct overall hybridization pattern that is different under different conditions (e.g., when harboring mutations in particular genes, in a disease state). Then this pattern of expression (an expression fingerprint), if reproducible and clearly differentiable in the different cases can be used as a very detailed diagnostic. It is not required that the pattern be fully interpretable, but just that it is specific for a particular cell state (and preferably of diagnostic and/or prognostic relevance).

Both customized and generic arrays can be used in drug safety studies. For example, if one is making a new antibiotic, then it should not significantly affect the expression profile for mammalian cells. The hybridization pattern can be used as a detailed measure of the effect of a drug on cells, for example, as a toxicological screen.

The sequence information provided by the hybridization pattern of a generic array can be used to identify genes encoding mRNAs hybridized to an array. Such methods can be performed using DNA nucleic acids of the invention as the target nucleic acids described in WO 97/27317. DNA nucleic acids can be denatured and then hybridized to the complementary regions of the probes, using standard conditions described in WO 97/27317. The hybridization pattern indicates which probes are complementary to nucleic acid strands in the sample. Comparison of the hybridization pattern of two samples indicates which probes hybridize to nucleic acid strands that derive from mRNAs that are differentially expressed between the two samples. These probes are of particular interest, because they contain complementary sequence to mRNA species subject to differential expression. The sequence of such probes is known and can be compared with sequences in databases to determine the identity of the full-length mRNAs subject to differential expression provided that such mRNAs have previously been sequenced. Alternatively, the sequences of probes can be used to design hybridization probes or primers for cloning the differentially expressed mRNAs. The differentially expressed mRNAs are typically cloned from the sample in which the mRNA of interest was expressed at the highest level. In some methods, database comparisons or cloning is facilitated by provision of additional sequence information beyond that inferable from probe sequence by template dependent extension as described above.

11. Screening for B Cell Activity Modulators (A) Candidate Bioactive Agents

Having identified a number of suitable expression profiles, the information is used in a wide variety of ways. In a preferred method, the expression profiles can be used in conjunction with high throughput screening techniques, to allow monitoring for expression profile genes after treatment with a candidate agent, Zlokarnik, et al., *Science* 279, 84–8 (1998), Heid et al., *Genome Res.* (1996) 6: 986. In a preferred method, the candidate agents are added to cells.

The term "candidate bioactive agent" or "drug candidate" or grammatical equivalents as used herein describes any molecule, e.g., protein, oligopeptide, small organic molecule, polysaccharide, polynucleotide, to be tested for bioactive agents that are capable of directly or indirectly altering the activity of a B cell. In preferred methods, the bioactive agents modulate the expression profiles, or expression profile nucleic acids or proteins provided herein. In a particularly preferred method, the candidate agents induce an immunosuppressive tolerant response, or maintain such a response as indicated, for example, by the effect of the agent on the expression profile, nucleic acids, proteins or B cell activity as further described below. Generally a plurality of assay mixtures are run in parallel with different agent concentrations to obtain a differential response to the various concentrations. Typically, one of these concentrations serves as a negative control, i.e., at zero concentration or below the level of detection.

Candidate agents encompass numerous chemical classes, though typically they are organic molecules, preferably small organic compounds having a molecular weight of more than 100 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents can be subjected to directed or random chemical modifications, such as acylation, alkylation, esterification, amidification to produce structural analogs.

In some preferred embodiment, the candidate bioactive agents are proteins. By "protein" herein is meant at least two covalently attached amino acids, which includes proteins, polypeptides, oligopeptides and peptides. The protein can be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains can be in either the (R) or the (S) configuration. In some preferred embodiment, the amino acids are in the (S) or L-configuration. If non-naturally occurring side chains are used, non-amino acid substituents can be used, for example to prevent or retard in vivo degradations.

In a preferred method, the candidate bioactive agents are naturally occurring proteins or fragments of naturally occurring proteins. Thus, for example, cellular extracts containing proteins, or random or directed digests of proteinaceous cellular extracts, can be used. In this way libraries of procaryotic and eucaryotic proteins can be made for screening in the methods of the invention. The libraries can be bacterial, fungal, viral, and mammalian proteins, with the latter being preferred, and human proteins.

In some methods, the candidate bioactive agents are peptides of from about 5 to about 30 amino acids, with from about 5 to about 20 amino acids being preferred, and from about 7 to about 15 being particularly preferred. The peptides can be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they can incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In some methods, the library can be fully randomized, with no sequence preferences or constants at any position. In other methods, the library can be biased. Some positions within the sequence are either held constant, or are selected from a limited number of possibilities. For example, in some methods, the nucleotides or amino acid residues are randomized within a defined class, for example, of hydrophobic amino acids, hydrophilic residues, sterically biased (either small or large) residues, towards the creation of nucleic acid binding domains, the creation of cysteines, for cross-linking, prolines for SH-3 domains, serines, threonines, tyrosines or histidines for phosphorylation sites, or to purines. In other methods, the candidate bioactive agents are nucleic acids, as defined above.

As described above generally for proteins, nucleic acid candidate bioactive agents can be naturally occurring nucleic acids, random nucleic acids, or "biased" random nucleic acids. For example, digests of procaryotic or eucaryotic genomes can be used as is outlined above for proteins.

In some methods, the candidate bioactive agents are organic chemical moieties.

(B) Drug Screening Methods

Several different drug screening methods can be accomplished to identify drugs or bioactive agents that modulate B cell activity. One such method is the screening of candidate agents that can induce a particular expression profile, thus preferably generating the associated phenotype. Candidate agents that can mimic or produce an expression profile similar to an immunosuppressive expression profile as shown herein is expected to result in the immunosuppressive phenotype. Similarly, candidate agents that can mimic or produce an expression profile similar to a tolerant expression profile as shown herein is expected to result in the tolerant phenotype. Thus, in some methods, candidate agents can be determined that mimic an expression profile or change one profile to another.

In other methods, after having identified the differentially expressed genes important in any one state, candidate agent screening can be run to alter the expression of individual genes. For example, particularly in the case of target genes whose presence or absence is unique between two states, screening for modulators of the target gene expression can be done.

In other methods, screening can be done to alter the biological function of the expression product of the differentially expressed gene. Again, having identified the importance of a gene in a particular state, screening for agents that bind and/or modulate the biological activity of the gene product can be performed as outlined below.

Thus, screening of candidate agents that modulate B cell activity either at the level of gene expression or protein level can be accomplished.

In some methods, a candidate agent can be administered to B cells in any state, that thus has an associated B cell activity expression profile. By "administration" or "contacting" herein is meant that the candidate agent is added to the cells in such a manner as to allow the agent to act upon the cell, whether by uptake and intracellular action, or by action at the cell surface. In some embodiments, nucleic acid encoding a proteinaceous candidate agent (i.e., a peptide) can be put into a viral construct such as a retroviral construct and added to the cell, such that expression of the peptide agent is accomplished; see PCT US97/01019, hereby expressly incorporated by reference.

Once the candidate agent has been administered to the cells, the cells can be washed if desired and are allowed to incubate under preferably physiological conditions for some period of time. The cells are then harvested and a new gene expression profile is generated, as outlined herein.

For example, activated B cells can be screened for agents that produce a tolerant phenotype. A change in at least one gene of the expression profile indicates that the agent has an effect on B cell activity. In a preferred method, an immunosuppressive tolerant profile is induced or maintained, before, during, and/or after stimulation with antigen. By defining such a signature for immunological tolerance, screens for new drugs that mimic the tolerance phenotype can be devised. With this approach, the drug target need not be known and need not be represented in the original expression screening platform, nor does the level of transcript for the target protein need to change. In some methods, the agent induces or maintains a profile which indicates a selective block immune response while still permitting tolerance to be actively (re)established. For example, in one such embodiment, the agent suppresses at least one of Egr-1, Egr-2, cmyc and c-fos while sparing upregulation of NAB2.

In some preferred methods, screens can be done on individual genes and gene products. After having identified a particular differentially expressed gene as important in a particular state, screening of modulators of either the expression of the gene or the gene product itself can be completed. The gene products of differentially expressed genes are sometimes referred to herein as "B lymphocyte modulator proteins" or BLMPs.

Thus, in some preferred methods, screening for modulators of expression of specific genes can be completed. This will be done as outlined above, but in general the expression of only one or a few genes are evaluated. In some methods, screens are designed to first find candidate agents that can bind to differentially expressed proteins, and then these agents can be used in other assays that evaluate the ability of the candidate agent to modulate differentially expressed activity. There are a number of different assays which can be completed, such as binding assays and activity assays.

In a preferred method, binding assays are performed. In general, purified or isolated gene product is used; that is, the gene products of one or more differentially expressed nucleic acids are made. Using the nucleic acids of the present invention which encode a differentially expressed protein in a B cell state, a variety of expression vectors can be made. The expression vectors can be either self-replicating extrachromosomal vectors or vectors which integrate into a host genome. Generally, these expression vectors include transcriptional and translational regulatory nucleic acid operably linked to the nucleic acid encoding a differentially expressed protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express a differentially expressed protein; for example, transcriptional and translational regulatory nucleic acid sequences from Bacillus are preferably used to express a differentially expressed protein in Bacillus. Numerous types of appropriate expression vectors, and suitable regulatory sequences are known in the art for a variety of host cells.

In general, the transcriptional and translational regulatory sequences can include, but are not limited to, promoter sequences, ribosomal binding sites, transcriptional start and stop sequences, translational start and stop sequences, and enhancer or activator sequences. In a preferred method, the regulatory sequences include a promoter and transcriptional start and stop sequences.

Promoter sequences encode either constitutive or inducible promoters. The promoters can be either naturally occurring promoters or hybrid promoters. Hybrid promoters, which combine elements of more than one promoter, are also known in the art, and are useful in the present invention.

In addition, the expression vector can comprise additional elements. For example, the expression vector can have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector can be directed to a specific locus in the host cell by selecting the appropriate homologous sequence for inclusion in the vector. Constructs for integrating vectors are well known in the art. Preferred methods to effect homologous recombination are described in PCT US93/03868 and PCT US98/05223, hereby incorporated by reference.

In some methods, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

The differentially expressed proteins of the present invention are produced by culturing a host cell transformed with an expression vector containing nucleic acid encoding a differentially expressed protein, under the appropriate conditions to induce or cause expression of a differentially expressed protein. The conditions appropriate for differentially expressed protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In some methods, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mamnmalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells. In some preferred methods, B cells are host cells as provided herein, which for example, include non-recombinant cell lines, such as primary cell lines. In addition, purified primary B cells derived from either transgenic or non-transgenic strains can also be used. The B cells can be in a particular state, or be induced to be in a particular state. The host cell can alternatively be a B cell known to have a B cell disorder.

In a preferred method, the differentially expressed proteins are expressed in mammalian cells. Mammalian expression systems can include retroviral systems. A mammalian promoter is any DNA sequence capable of binding mammalian RNA polymerase and initiating the downstream (3') transcription of a coding sequence for differentially expressed protein into mRNA. A promoter will have a transcription initiating region, which is usually placed proximal to the 5' end of the coding sequence, and a TATA box, using a located 25–30 base pairs upstream of the transcription initiation site. The TATA box is thought to direct RNA polymerase II to begin RNA synthesis at the correct site. A mammalian promoter will also contain an upstream promoter element (enhancer element), typically located within 100 to 200 base pairs upstream of the TATA box. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-translational cleavage and polyadenylation. Examples of transcription terminator and polyadenlytion signals include those derived form SV40.

The methods of introducing nucleic acid into mammalian hosts, as well as other hosts, is well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In some methods, differentially expressed proteins are expressed in bacterial systems which are well known in the art.

In other methods, differentially expressed proteins can be produced in insect cells. Expression vectors for the transformation of insect cells, and in particular, baculovirus-based expression vectors, are well known in the art.

In some methods, differentially expressed proteins are produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe*, and *Yarrowia lipolytica*.

A differentially expressed protein can also be made as a fusion protein, using techniques well known in the art. For example, for the creation of monoclonal antibodies, if the desired epitope is small, the differentially expressed protein can be fused to a carrier protein to form an immunogen. Alternatively, a differentially expressed protein can be made as a fusion protein to increase expression. For example, when a differentially expressed protein is a differentially expressed peptide, the nucleic acid encoding the peptide can be linked to other nucleic acid for expression purposes. Similarly, differentially expressed proteins of the invention an be linked to protein labels, such as green fluorescent protein (GFP), red fluorescent protein (RFP), yellow fluorescent protein (YFP), and blue fluorescent protein (BFP).

Preferably, the proteins are recombinant. A "recombinant protein" is a protein made using recombinant techniques, i.e., through the expression of a recombinant nucleic acid as depicted above. A recombinant protein is distinguished from naturally occurring protein by at least one or more characteristics. For example, the protein can be isolated or purified away from some or all of the proteins and compounds with which it is normally associated in its wild type host, and thus can be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a differentially expressed protein from one organism in a different organism or host cell. Alternatively, the protein can be made at a significantly higher concentration than is normally seen, through the use of a inducible promoter or high expression promoter, such that the protein is made at increased concentration levels. Alternatively, the protein can be in a form not normally found in nature, as in the addition of an epitope tag or amino acid substitutions, insertions and deletions, as discussed below.

In some preferred methods, when the differentially expressed protein is to be used to generate antibodies, the protein must share at least one epitope or determinant with the full length transcription product of the differentially expressed nucleic acids shown herein. By "epitope" or "determinant" herein is meant a portion of a protein which will generate and/or bind an antibody. Thus, in most instances, antibodies made to a smaller protein should be able to bind to the full length protein. In a preferred embodiment, the epitope is unique; that is, antibodies generated to a unique epitope show little or no cross-reactivity.

In some preferred methods, the antibodies provided herein can be capable of reducing or eliminating the biological flnction of a differentially expressed protein, as is described below. The addition of antibodies (either polyclonal or preferably monoclonal) to the protein (or cells containing the differentially expressed protein) can reduce or eliminate the protein's activity. Generally, at least a 25% decrease in activity is preferred, with at least about 50% being particularly preferred and about a 95–100% decrease being especially preferred.

In addition, the proteins can be variant proteins, comprising one more amino acid substitutions, insertions and deletions.

In a preferred method, a differentially expressed protein is purified or isolated after expression. Differentially expressed proteins can be isolated or purified in a variety of ways. Standard purification methods include electrophoretic, molecular, immunological and chromatographic techniques, including ion exchange, hydrophobic, affinity, and reverse-phase HPLC chromatography, and chromatofocusing. For example, a differentially expressed protein can be purified using a standard anti-differentially expressed protein antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the differentially expressed protein. In some instances no purification will be necessary.

Once the gene product of the differentially expressed gene is made, binding assays can be done. These methods comprise combining a differentially expressed protein and a candidate bioactive agent, and determining the binding of the candidate agent to the differentially expressed protein. Preferred methods utilize a human differentially expressed protein, although other mammalian proteins can also be used, including rodents (mice, rats, hamsters, guinea pigs), farm animals (cows, sheep, pigs, horses) and primates. These latter methods can be preferred for the development of animal models of human disease. In some methods, variant or derivative differentially expressed proteins can be used, including deletion differentially expressed proteins as outlined above.

The assays herein utilize differentially expressed proteins as defined herein. In some assays, portions of differentially expressed proteins can be utilized. In other assays, portions having differentially expressed activity can be used. In addition, the assays described herein can utilize either isolated differentially expressed proteins or cells comprising the differentially expressed proteins. In some methods, the differentially expressed protein or the candidate agent is non-difflisably bound to an insoluble support having isolated sample receiving areas (e.g., a microtiter plate or an array). The insoluble supports can be made of any composition to which the compositions can be bound, is readily separated from soluble material, and is otherwise compatible with the overall method of screening. The surface of such supports can be solid or porous and of any convenient shape. Examples of suitable insoluble supports include microtiter plates, arrays, membranes and beads. These are typically made of glass, plastic (e.g., polystyrene), polysaccharides, nylon or nitrocellulose, and teflon™. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface. Following binding of the protein or agent, excess unbound material is removed by washing. The sample receiving areas can then be blocked through incubation with bovine serum albumin (BSA), casein or other innocuous protein or other moiety. Also included in this invention are screening assays wherein solid supports are not used.

In other methods, the differentially expressed protein is bound to the support, and a candidate bioactive agent is added to the assay. Alternatively, the candidate agent is bound to the support and the differentially expressed protein is added. Novel binding agents include specific antibodies, non-natural binding agents identified in screens of chemical libraries, and peptide analogs. Of particular interest are screening assays for agents that have a low toxicity for human cells. A wide variety of assays can be used for this purpose, including labeled in vitro protein-protein binding assays, electrophoretic mobility shift assays, immunoassays for protein binding, functional assays (such as phosphorylation assays) and the like.

The determination of the binding of the candidate bioactive agent to a differentially expressed protein can be done in a number of ways. In some methods, the candidate bioactive agent is labeled, and binding determined directly. For example, this can be done by attaching all or a portion of a differentially expressed protein to a solid support, adding a labeled candidate agent (for example a fluorescent label), washing off excess reagent, and determining whether the label is present on the solid support. Various blocking and washing steps can be utilized.

By "labeled" herein is meant that the compound is either directly or indirectly labeled with a label which provides a detectable signal, e.g., radioisotope, fluorescers, enzyme, antibodies, particles such as magnetic particles, chemiluminescers, or specific binding molecules. Specific binding molecules include pairs, such as biotin and streptavidin, digoxin and antidigoxin. For the specific binding members, the complementary member would normally be labeled with a molecule which provides for detection, in accordance with known procedures, as outlined above. The label can directly or indirectly provide a detectable signal.

In some methods, only one of the components is labeled. For example, the proteins (or proteinaceous candidate agents) can be labeled at tyrosine positions using $^{125}$I, or with fluorophores. Alternatively, more than one component can be labeled with different labels; using $^{125}$I for the proteins, for example, and a fluorophor for the candidate agents.

In other methods, the binding of the candidate bioactive agent is determined through the use of competitive binding assays. In this method, the competitor is a binding moiety known to bind to the target molecule such as an antibody, peptide, binding partner, or ligand. Under certain circumstances, there can be competitive binding as between the bioactive agent and the binding moiety, with the binding moiety displacing the bioactive agent. This assay can be used to determine candidate agents which interfere with binding between differentially expressed proteins and the competitor.

In some methods, the candidate bioactive agent is labeled. Either the candidate bioactive agent, or the competitor, or both, is added first to the protein for a time sufficient to allow binding, if present. Incubations can be performed at any temperature which facilitates optimal activity, typically between 4 and 40° C. Incubation periods are selected for optimum activity, but can also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In other methods, the competitor is added first, followed by the candidate bioactive agent. Displacement of the competitor is an indication that the candidate bioacfive agent is binding to the differentially expressed protein and thus is capable of binding to, and potentially modulating, the activity of the differentially expressed protein. In this method, either component can be labeled. For example, if the competitor is labeled, the presence of label in the wash solution indicates displacement by the agent. Alternatively, if the candidate bioactive agent is labeled, the presence of the label on the support indicates displacement.

In other methods, the candidate bioactive agent is added first, with incubation and washing, followed by the competitor. The absence of binding by the competitor can indicate that the bioactive agent is bound to the differentially expressed protein with a higher affinity. Thus, if the candidate bioactive agent is labeled, the presence of the label on the support, coupled with a lack of competitor binding, can indicate that the candidate agent is capable of binding to the differentially expressed protein.

Competitive binding methods can also be run as differential screens. These methods can comprise a differentially expressed protein and a competitor in a first sample. A second sample comprises a candidate bioactive agent, a differentially expressed protein and a competitor. The binding of the competitor is determined for both samples, and a change, or difference in binding between the two samples indicates the presence of an agent capable of binding to the differentially expressed protein and potentially modulating its activity. If the binding of the competitor is different in the second sample relative to the first sample, the agent is capable of binding to the differentially expressed protein.

Other methods utilize differential screening to identify drug candidates that bind to the native differentially expressed protein, but cannot bind to modified differentially expressed proteins. The structure of the differentially expressed protein can be modeled, and used in rational drug design to synthesize agents that interact with that site. Drug candidates that affect differentially expressed bioactivity are also identified by screening drugs for the ability to either enhance or reduce the activity of the protein.

In some methods, screening for agents that modulate the activity of differentially expressed proteins are performed. In general, this will be done on the basis of the known biological activity of the differentially expressed protein. In these methods, a candidate bioactive agent is added to a sample of the differentially expressed protein, as above, and an alteration in the biological activity of the protein is determined. "Modulating the activity" includes an increase in activity, a decrease in activity, or a change in the type or kind of activity present. Thus, in these methods, the candidate agent should both bind to differentially expressed (although this may not be necessary), and alter its biological or biochemical activity as defined herein. The methods include both in vitro screening methods, as are generally outlined above, and in vivo screening of cells for alterations in the presence, distribution, activity or amount of the differentially expressed protein.

Some methods comprise combining a differentially expressed sample and a candidate bioactive agent, then evaluating the effect on B cell activity. By "differentially expressed activity" or grammatical equivalents herein is meant one of B cell biological activities, including, but not limited to, its ability to affect suppression, tolerance and activation. One activity herein is the capability to bind to a target gene, or modulate an expression profile. Preferably, expression profiles are induced or maintained and/or the desired B cell state is induced or maintained.

In other methods, the activity of the differentially expressed protein is increased; in other methods, the activity of the differentially expressed protein is decreased. Thus, bioactive agents that are antagonists are preferred in some methods, and bioactive agents that are agonists can be preferred in other methods.

The invention provides methods for screening for bioactive agents capable of modulating the activity of a differentially expressed protein. These methods comprise adding a candidate bioactive agent, as defined above, to a cell comprising differentially expressed proteins. Preferred cell types include almost any cell. The cells contain a recombinant nucleic acid that encodes a differentially expressed protein. In a preferred method, a library of candidate agents are tested on a plurality of cells. The effect of the candidate agent on B cell activity is then evaluated.

Positive controls and negative controls can be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples can be counted in a scintillation counter to determine the amount of bound compound.

A variety of other reagents can be included in the screening assays. These include reagents like salts, neutral proteins (e.g., albumin and detergents) which can be used to facilitate optimal protein-protein binding and/or reduce non-specific or background interactions. Reagents that otherwise improve the efficiency of the assay, (such as protease inhibitors, nuclease inhibitors, anti-microbial agents) can also be used. The mixture of components can be added in any order that provides for the requisite binding.

The components provided herein for the assays provided herein can also be combined to form kits. The kits can be based on the use of the protein and/or the nucleic acid encoding the differentially expressed proteins. Assays regarding the use of nucleic acids are further described below.

(C) Animal Models

In a preferred method, nucleic acids which encode differentially expressed proteins or their modified forms can also be used to generate either transgenic animals, including "knock-in" and "knock out" animals which, in turn, are useful in the development and screening of therapeutically useful reagents. A non-human transgenic animal (e.g., a mouse or rat) is an animal having cells that contain a transgene, which transgene is introduced into the animal or an ancestor of the animal at a prenatal, e.g., an embryonic stage. A transgene is a DNA which is integrated into the genome of a cell from which a transgenic animal develops, and can include both the addition of all or part of a gene or the deletion of all or part of a gene. In some methods, cDNA encoding a differentially expressed protein can be used to clone genomic DNA encoding a differentially expressed protein in accordance with established techniques and the genomic sequences used to generate transgenic animals that contain cells which either express (or overexpress) or suppress the desired DNA. Methods for generating transgenic animals, particularly animals such as mice or rats, have become conventional in the art and are described, for example, in U.S. Pat. Nos. 4,736,866 and 4,870,009. Typically, particular cells would be targeted for a differentially expressed protein transgene incorporation with tissue-specific enhancers. Transgenic animals that include a copy of a transgene encoding a differentially expressed protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition. Similarly, non-human homologues of a differentially expressed protein can be used to construct a transgenic animal comprising a differentially expressed protein "knock out" animal which has a defective or altered gene encoding a differentially expressed protein as a result of homologous recombination between the endogenous gene encoding a differentially expressed protein and altered genomic DNA encoding a differentially expressed protein introduced into an embryonic cell of the animal. For example, cDNA encoding a differentially expressed protein can be used to clone genomic DNA encoding a differentially expressed protein in accordance with established techniques. A portion of the genomic DNA encoding a differentially expressed protein can be deleted or replaced with another gene, such as a gene encoding a selectable marker which can be used to monitor integration. Typically, several kilobases of unaltered flanking DNA (both at the 5' and 3' ends) are included in the vector (see, e.g., Thomas and Capecchi, *Cell* (1987) 51: 503 for a description of homologous recombination vectors). The vector is introduced into an embryonic stem cell line (e.g., by electroporation) and cells in which the introduced DNA has homologously recombined with the endogenous DNA are selected (see, e.g., Li et al., *Cell* (1992) 69: 915). The selected cells are then injected into a blastocyst of an animal (e.g., a mouse or rat) to form aggregation chimeras (see, e.g., Bradley, in *Teratocarcinomas and Embryonic Stem Cells: A Practical Approach*, E. J. Robertson, ed. (IRL, Oxford, 1987), pp. 113–152). A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of a differentially expressed protein polypeptide.

Animal models for B cell related disorders, or having a particular state of B cell activity can include, for example, genetic models. For example, such animal models can include the nonobese diabetic (NOD) mouse (see, e.g., McDuffie, M., *Curr Opin Immunol.* (1998) 10(6):704–9; Tochino, Y., *Crit Rev Immunol* (1987) 8(1): 49–81), and experimental autoimmune encephalomyelitis (EAE) (see, e.g., Wong, F. S., *Immunol Rev* (1999) 169: 93-104). See also Schwartz, R. S. and Datta, S. K., *Autoimmunity and Autoimmune Diseases*, Ch. 31, in *Fundamental Immunology*, Paul, W. E. (ed.) (Raven Press 1989). Other models can include studies involving transplant rejection.

Animal models exhibiting B cell related disorder-like symptoms can be engineered by utilizing, for example, differentially expressed sequences in conjunction with techniques for producing transgenic animals that are well known to those of skill in the art. For example, gene sequences can be introduced into, and overexpressed in, the genome of the animal of interest, or, if endogenous target gene sequences are present, they can either be overexpressed or, alternatively, can be disrupted in order to underexpress or inactivate target gene expression.

In order to overexpress a target gene sequence, the coding portion of the target gene sequence can be ligated to a regulatory sequence which is capable of driving gene expression in the animal and cell type of interest. Such regulatory regions will be well known to those of skill in the art, and can be utilized in the absence of undue experimentation.

For underexpression of an endogenous target gene sequence, such a sequence can be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target sequence into the animal's genome.

Animals of any species, including, but not limited to, mice, rats, rabbits, guinea pigs, pigs, micro-pigs, goats, and non-human primates, e.g., baboons, monkeys, and chimpanzees can be used to generate animal models of B cell related disorders or being a perpetually desired state of the B cell.

(D) Nucleic Acid Based Therapeutics

Nucleic acids encoding differentially expressed polypeptides, antagonists or agonists can also be used in gene therapy. Broadly speaking, a gene therapy vector is an exogenous polynucleotide which produces a medically useful phenotypic effect upon the mammalian cell(s) into which it is transferred. A vector can or can not have an origin of replication. For example, it is useful to include an origin of replication in a vector for propagation of the vector prior to administration to a patient. However, the origin of replication can often be removed before administration if the vector is designed to integrate into host chromosomal DNA or bind to host mRNA or DNA. Vectors used in gene therapy can be viral or nonviral. Viral vectors are usually introduced into a patient as components of a virus. Nonviral vectors, typically dsDNA, can be transferred as naked DNA or associated with a transfer-enhancing vehicle, such as a receptor-recognition protein, lipoamine, or cationic lipid.

(1) Viral-Based Methods

Viral vectors, such as retroviruses, adenoviruses, adenoassociated viruses and herpes viruses, are often made up of two components, a modified viral genome and a coat structure surrounding it (see generally Smith et al., *Ann. Rev. Microbiol.* (1995) 49,807–838; this reference and all references cited therein are incorporated herein by reference), although sometimes viral vectors are introduced in naked form or coated with proteins other than viral proteins. Most current vectors have coat structures similar to a wildtype virus. This structure packages and protects the viral nucleic acid and provides the means to bind and enter target cells.

However, the viral nucleic acid in a vector designed for gene therapy is changed in many ways. The goals of these changes are to disable growth of the virus in target cells while maintaining its ability to grow in vector form in available packaging or helper cells, to provide space within the viral genome for insertion of exogenous DNA sequences, and to incorporate new sequences that encode and enable appropriate expression of the gene of interest. Thus, vector nucleic acids generally comprise two components: essential cis-acting viral sequences for replication and packaging in a helper line and the transcription unit for the exogenous gene. Other viral functions are expressed in trans in a specific packaging or helper cell line.

(a) Retroviruses

Retroviruses comprise a large class of enveloped viruses that contain single—stranded RNA as the viral genome. During the normal viral life cycle, viral RNA is reverse-transcribed to yield double-stranded DNA that integrates into the host genome and is expressed over extended periods. As a result, infected cells shed virus continuously without apparent harm to the host cell. The viral genome is small (approximately 10 kb), and its prototypical organization is extremely simple, comprising three genes encoding gag, the group specific antigens or core proteins; pol, the reverse transcriptase; and env, the viral envelope protein. The termini of the RNA genome are called long terminal repeats (LTRs) and include promoter and enhancer activities and sequences involved in integration. The genome also includes a sequence required for packaging viral RNA and splice acceptor and donor sites for generation of the separate envelope mRNA. Most retroviruses can integrate only into replicating cells, although human immunodeficiency virus (HIV) appears to be an exception. This property restricts the use of retroviruses as vectors for gene therapy.

Retrovirus vectors are relatively simple, containing the 5' and 3' LTRs, a packaging sequence, and a transcription unit composed of the gene or genes of interest, which is typically an expression cassette. To grow such a vector, one must provide the missing viral functions in trans using a so-called packaging cell line. Such a cell is engineered to contain integrated copies of gag, pol, and env but to lack a packaging signal so that no helper virus sequences become encapsidated. Additional features added to or removed from the vector and packaging cell line reflect attempts to render the vectors more efficacious or reduce the possibility of contamination by helper virus.

The main advantage of retroviral vectors is that they integrate and are therefore potentially capable of long-term expression. They can be grown in relatively large amounts, but care is needed to ensure the absence of helper virus.

(b) Adenoviruses

Adenoviruses comprise a large class of nonenveloped viruses containing linear double-stranded DNA. The normal life cycle of the virus does not require dividing cells and involves productive infection in permissive cells during which large amounts of virus accumulate. The productive infection cycle takes about 32-36 hours in cell culture and comprises two phases, the early phase, prior to viral DNA synthesis, and the late phase, during which structural proteins and viral DNA are synthesized and assembled into virions. In general, adenovirus infections are associated with mild disease in humans.

Adenovirus vectors are somewhat larger and more complex than retrovirus or AAV vectors, partly because only a small fraction of the viral genome is removed from most current vectors. If additional genes are removed, they are provided in trans to produce the vector, which so far has proved difficult. Instead, two general types of adenovirus-based vectors have been studied, E3-deletion and E1-deletion vectors. Some viruses in laboratory stocks of wildtype lack the E3 region and can grow in the absence of helper. This ability does not mean that the E3 gene products are not necessary in the wild, only that replication in cultured cells does not require them. Deletion of the E3 region allows insertion of exogenous DNA sequences to yield vectors capable of productive infection and the transient synthesis of relatively large amounts of encoded protein.

Deletion of the E1 region disables the adenovirus, but such vectors can still be grown because there exists an established human cell line (called "293") that contains the E1 region of Ad5 and that constitutively expresses the E1 proteins. Most recent gene therapy applications involving adenovirus have utilized E1 replacement vectors grown in 293 cells.

The main advantages of adenovirus vectors are that they are capable of efficient episomal gene transfer in a wide range of cells and tissues and that they are easy to grow in large amounts. The main disadvantage is that the host response to the virus appears to limit the duration of expression and the ability to repeat dosing, at least with high doses of first-generation vectors.

(c) Adeno-Associated Virus (AAV)

AAV is a small, simple, nonautonomous virus containing linear single-stranded DNA. See Muzycka, *Current Topics Microbiol. Immunol.* (1992) 158, 97–129; this reference and all references cited therein are incorporated herein by reference. The virus requires co-infection with adenovirus or certain other viruses in order to replicate. AAV is widespread in the human population, as evidenced by antibodies to the virus, but it is not associated with any known disease. AAV genome organization is straightforward, comprising only two genes: rep and cap. The termini of the genome comprises terminal repeats (ITR) sequences of about 145 nucleotides.

AAV-based vectors typically contain only the ITR sequences flanking the transcription unit of interest. The length of the vector DNA cannot greatly exceed the viral genome length of 4680 nucleotides. Currently, growth of AAV vectors is cumbersome and involves introducing into the host cell not only the vector itself but also a plasmid encoding rep and cap to provide helper functions. The helper plasmid lacks ITRs and consequently cannot replicate and package. In addition, helper virus such as adenovirus is often required. The potential advantage of AAV vectors is that they appear capable of long-term expression in nondividing cells, possibly, though not necessarily, because the viral DNA integrates. The vectors are structurally simple, and they can therefore provoke less of a host-cell response than adenovirus. A major limitation at present is that AAV vectors are extremely difficult to grow in large amounts.

(2) Non-Viral Gene Transfer Methods

Nonviral nucleic acid vectors used in gene therapy include plasmids, RNAs, antisense oligonucleotides (e.g., methylphosphonate or phosphorothiolate), polyamide nucleic acids, and yeast artificial chromosomes (YACs). Such vectors typically include an expression cassette for expressing a protein or RNA. The promoter in such an expression cassette can be constitutive, cell type-specific, stage-specific, and/or modulatable (e.g., by hormones such as glucocorticoids; MMTV promoter). Transcription can be increased by inserting an enhancer sequence into the vector. Enhancers are cis-acting sequences of between 10 to 300 bp that increase transcription by a promoter. Enhancers can effectively increase transcription when either 5' or 3' to the transcription unit. They are also effective if located within an intron or within the coding sequence itself. Typically, viral enhancers are used, including SV40 enhancers, cytomegalovirus enhancers, polyoma enhancers, and adenovirus enhancers. Enhancer sequences from mammalian systems are also commonly used, such as the mouse immunoglobulin heavy chain enhancer.

Gene therapy vectors of all kinds can also include a selectable marker gene. Examples of suitable markers include, the dihydrofolate reductase gene (DHFR), the thymidine kinase gene (TK), or prokaryotic genes conferring drug resistance, gpt (xanthine-guanine phosphoribosyltransferase, which can be selected for with mycophenolic acid; neo (neomycin phosphotransferase), which can be selected for with G418, hygromycin, or puromycin; and DHFR (dihydrofolate reductase), which can be selected for with methotrexate (Mulligan & Berg, *Proc. Nati. Acad. Sci. U.S.A.* (1981) 78, 2072; Southern & Berg, *J. Mol. Appl. Genet.* (1982) 1, 327).

Before integration, the vector has to cross many barriers which can result in only a very minor fraction of the DNA ever being expressed. Limitations to high level gene expression include: loss of vector due to nucleases present in blood and tissues; inefficient entry of DNA into a cell; inefficient entry of DNA into the nucleus of the cell and preference of DNA for other compartments; lack of DNA stability in the nucleus (factor limiting nuclear stability can differ from those affecting other cellular and extracellular compartments), efficiency of integration into the chromosome; and site of integration.

These potential losses of efficiency can be addressed by including additional sequences in a nonviral vector besides the expression cassette from which the product effecting therapy is to be expressed. The additional sequences can have roles in conferring stability both outside and within a cell, mediating entry into a cell, mediating entry into the nucleus of a cell and mediating integration within nuclear DNA. For example, aptamer-like DNA structures, or other protein binding sites can be used to mediate binding of a vector to cell surface receptors or to serum proteins that bind to a receptor thereby increasing the efficiency of DNA transfer into the cell.

Other DNA sequences can directly or indirectly result in avoidance of certain compartments and preference for other compartments, from which escape or entry into the nucleus is more efficient. Other DNA sites and structures directly or indirectly bind to receptors in the nuclear membrane or to other proteins that go into the nucleus, thereby facilitating nuclear uptake of a vector. Other DNA sequences directly or indirectly affect the efficiency of integration. For integration by homologous recombination, important factors are the degree and length of homology to chromosomal sequences, as well as the frequency of such sequences in the genome (e.g., alu repeats). The specific sequence mediating homologous recombination is also important, since integration occurs much more easily in transcriptionally active DNA. Methods and materials for constructing homologous targeting constructs are described by e.g., Mansour et al., *Nature* (1988) 336: 348; Bradley et al., *Bio/Technology* (1992) 10: 534.

For nonhomologous, illegitimate and site-specific recombination, recombination is mediated by specific sites on the therapy vector which interact with cell encoded recombination proteins (e.g., cre/lox and flp/frt systems). For example Baubonis & Sauer, *Nuc. Acids Res.* (1993) 21, 2025–2029 report that a vector including a loxP site becomes integrated at a loxP site in chromosomal DNA in the presence of cre enzyme.

Nonviral vectors encoding products useful in gene therapy can be introduced into an animal by means such as lipofection, biolistics, virosomes, liposomes, immunoliposomes, polycation: nucleic acid conjugates, naked DNA, artificial virions, agent-enhanced uptake of DNA, ex vivo transduction. Lipofection is described in e.g., U.S. Pat. Nos. 5,049,386, 4,946,787; and 4,897,355) and lipofection reagents are sold commercially (e.g., TRANSFECTAM™ AND LIPFECTIN™). Cationic and neutral lipids that are suitable for efficient receptor-recognition lipofection of polynucleotides include those of Felgner, WO 91/17424, WO 91/16024.

Unlike existing viral-based gene therapy vectors which can only incorporate a relatively small non-viral polynucleotide sequence into the viral genome because of size limitations for packaging virion particles, naked DNA or lipofection complexes can be used to transfer large (e.g., 50–5,000 kb) exogenous polynucleotides into cells. This property of nonviral vectors is particularly advantageous since many genes which can be delivered by therapy span over 100 kilobases (e.g., amyloid precursor protein (APP) gene, Huntington's chorea gene) and large homologous targeting constructs or transgenes can be required for efficient integration. Optionally, such large genes can be delivered to target cells as two or more fragments and reconstructed by homologous recombination within a cell (see WO 92/03917).

(3) Applications of Gene Therapy

Gene therapy vectors can be delivered in vivo by administration to an individual patient, typically by systemic administration (e.g., intravenous, intraperitoneal, intramuscular, subdermal, or intracranial infusion) or topical application. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

12. Diagnostic Methods

In addition to assays, the creation of animal models, and nucleic acid based therepeutics, identification of important differentially expressed genes allows the use of these genes in diagnosis (e.g., diagnosis of cell states and abnormal B cell conditions). Disorders based on mutant or variant differentially expressed genes can be determined. The invention also provides methods for identifying cells containing variant differentially expressed genes comprising determining all or part of the sequence of at least one endogeneous differentially expressed genes in a cell. As will be appreciated by those in the art, this can be done using any number of sequencing techniques. The invention also provides methods of identifying the differentially expressed genotype of an individual comprising determining all or part of the sequence of at least one differentially expressed gene of the individual. This is generally done in at least one tissue of the individual, and can include the evaluation of a number of tissues or different samples of the same tissue. The method can include comparing the sequence of the sequenced differentially expressed gene to a known differentially expressed gene, i.e., a wild-type gene.

The sequence of all or part of the differentially expressed gene can then be compared to the sequence of a known differentially expressed gene to determine if any differences exist. This can be done using any number of known sequence identity programs, such as Bestfit, and others outlined herein. In some preferred methods, the presence of a difference in the sequence between the differentially expressed gene of the patient and the known differentially expressed gene is indicative of a disease state or a propensity for a disease state, as outlined herein.

Similarly, diagnosis of B cell states can be done using the methods of the invention. By evaluating the gene expression profile of B cells from a patient, the B cell state can be determined. This is particularly useful to verify the action of a drug, for example an immunosuppressive drug. Other methods comprise administering the drug to a patient and removing a cell sample, particularly of B cells, from the patient. The gene expression profile of the cell is then evaluated, as outlined herein, for example by comparing it to the expression profile from an equivalent sample from a healthy individual. In this manner, both the efficacy (i.e., whether the correct expression profile is being generated from the drug) and the dose (is the dosage correct to result in the correct expression profile) can be verified.

The present discovery relating to the role of differentially expressed in B cells thus provides methods for inducing or maintaining differing B cell states. In a preferred method, the differentially expressed proteins, and particularly differentially expressed fragments, are useful in the study or treatment of conditions which are mediated by B cell activity, i.e., to diagnose, treat or prevent B cell-mediated disorders. Thus, "B cell mediated disorders" or "disease states" can include conditions involving, for example, arthritis, diabetes, or multiple sclerosis.

Methods of modulating B cell activity in cells or organisms are provided. Some methods comprise administering to a cell an anti-differentially expressed antibody or other agent identified herein or by the methods provided herein, that reduces or eliminates the biological activity of the endogeneous differentially expressed protein. Alternatively, the methods comprise administering to a cell or organism a recombinant nucleic acid encoding a differentially expressed protein or modulator including anti-sense nucleic acids. As will be appreciated by those in the art, this can be accomplished in any number of ways. In some preferred methods, the activity of differentially expressed is increased by increasing the amount of differentially expressed in the cell, for example by overexpressing the endogeneous differentially expressed or by administering a differentially expressed gene, using known gene therapy techniques, for example. In a preferred method, the gene therapy techniques include the incorporation of the exogenous gene using enhanced homologous recombination (EHR), for example as described in PCT/US93/03868, hereby incorporated by reference in its entirety.

In some methods, the invention provides methods for diagnosing an B cell activity related condition in an individual. The methods comprise measuring the activity of differentially expressed protein in a tissue from the individual or patient, which can include a measurement of the amount or specific activity of the protein. This activity is compared to the activity of differentially expressed from either a unaffected second individual or from an unaffected tissue from the first individual. When these activities are different, the first individual can be at risk for an B cell activity mediated disorder.

Furthermore, nucleotide sequences encoding a differentially expressed protein can also be used to construct hybridization probes for mapping the gene which encodes that differentially expressed protein and for the genetic analysis of individuals with genetic disorders. The nucleotide sequences provided herein can be mapped to a chromosome and specific regions of a chromosome using known techniques, such as in situ hybridization, linkage analysis against known chromosomal markers, and hybridization screening with libraries.

13. Antibodies

In some methods, the differentially expressed proteins of the present invention can be used to generate polyclonal and monoclonal antibodies to differentially expressed proteins, which are useful as described herein. A number of immunogens are used to produce antibodies that specifically bind differentially expressed polypeptides. Full-length differentially expressed polypeptides are suitable immunogens. Typically, the immunogen of interest is a peptide of at least about 3 amino acids, more typically the peptide is at least 5 amino acids in length, preferably, the fragment is at least 10 amino acids in length and more preferably the fragment is at least 15 amino acids in length. The peptides can be coupled to a carrier protein (e.g., as a fusion protein), or are recombinantly expressed in an immunization vector. Antigenic determinants on peptides to which antibodies bind are typically 3 to 10 amino acids in length. Naturally occurring polypeptides are also used either in pure or impure form. Recombinant polypeptides are expressed in eukaryotic or prokaryotic cells and purified using standard techniques. The polypeptide, or a synthetic version thereof, is then injected into an animal capable of producing antibodies. Either monoclonal or polyclonal antibodies can be generated for subsequent use in immunoassays to measure the presence and quantity of the polypeptide.

These antibodies find use in a number of applications. For example, the differentially expressed antibodies can be coupled to standard affinity chromatography columns and used to purify differentially expressed proteins as further described below. The antibodies can also be used as blocking polypeptides, as outlined above, since they will specifically bind to the differentially expressed protein.

The anti-differentially expressed protein antibodies can comprise polyclonal antibodies. Methods for producing polyclonal antibodies are known to those of skill in the art. In brief, an immunogen, preferably a purified polypeptide, a polypeptide coupled to an appropriate carrier (e.g., GST and keyhole limpet hemocyanin), or a polypeptide incorporated into an immunization vector such as a recombinant vaccinia virus (see, U.S. Pat. No. 4,722,848) is mixed with an adjuvant and animals are immunized with the mixture. The animal's immune response to the immunogen preparation is monitored by taking test bleeds and determining the titer of reactivity to the polypeptide of interest. When appropriately high titers of antibody to the immunogen are obtained, blood is collected from the animal and antisera are prepared. Further fractionation of the antisera to enrich for antibodies reactive to the polypeptide is performed where desired. See, e.g., Coligan (1991) CURRENT PROTOCOLS IN IMMUNOLOGY Wiley/Greene, NY; and Harlow and Lane (1989) ANTIBODIES: A LABORATORY MANUAL Cold Spring Harbor Press, NY.

Antibodies, including binding fragments and single chain recombinant versions thereof, against predetermined fragments of differentially expressed proteins are raised by immunizing animals, e.g., with conjugates of the fragments with carrier proteins as described above.

The anti-differentially expressed protein antibodies can, alternatively, be monoclonal antibodies. The monoclonal antibodies are prepared from cells secreting the desired antibody. These antibodies are screened for binding to normal or modified polypeptides, or screened for agonistic or antagonistic activity, e.g., activity mediated through the differentially expressed proteins. In some instances, it is desirable to prepare monoclonal antibodies from various mammalian hosts, such as mice, rodents, primates, and humans. Description of techniques for preparing such monoclonal antibodies are found in, e.g., Stites et al. (eds.) BASIC AND CLINICAL IMMUNOLOGY (4th ed.) Lange Medical Publications, Los Altos, Calif., and references cited therein; Harlow and Lane, Supra; Goding (1986) *Monoclonal Antibodies: Principles and Practice* (2d ed.) Academic Press, New York, N.Y.; and Kohler and Milstein (1975) *Nature* 256: 495-497.

The immunizing agent will typically include the differentially expressed protein polypeptide or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59–103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, Marcel Dekker, Inc., New York, (1987) pp. 51–63).

The culture medium in which the hybridoma cells are cultured can then be assayed for the presence of monoclonal antibodies directed against differentially expressed protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.* 107:220 (1980).

After the desired hybridoma cells are identified, the clones can be subdloned by limiting dilution procedures and grown by standard methods (Goding, supra). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Other suitable techniques involve selection of libraries of recombinant antibodies in phage or similar vectors. See, Huse et al. (1989) *Science* 246: 1275–1281; and Ward, et al. (1989) *Nature* 341: 544–546.

Also, recombinant immunoglobulins may be produced. See, U.S. Pat. No. 4,816,567 (Cabilly); and Queen et al. (1989) *Proc. Nat'l Acad. Sci. USA* 86: 10029–10033.

Briefly, nucleic acids encoding light and heavy chain variable regions, optionally linked to constant regions, are inserted into expression vectors. The light and heavy chains can be cloned in the same or different expression vectors. The DNA segments encoding antibody chains are operably linked to control sequences in the expression vector(s) that ensure the expression of antibody chains. Such control sequences include a signal sequence, a promoter, an enhancer, and a transcription termination sequence. Expression vectors are typically replicable in the host organisms either as episomes or as an integral part of the host chromosome.

*E. coli* is one procaryotic host particularly for expressing antibodies of the present invention. Other microbial hosts suitable for use include bacilli, such as *Bacillus subtilus*, and other enterobacteriaceae, such as *Salmonella, Serratia*, and various *Pseudomonas species*. In these prokaryotic hosts, one can also make expression vectors, which typically contain expression control sequences compatible with the host cell (e.g., an origin of replication) and regulatory sequences such as a lactose promoter system, a tryptophan (trp) promoter system, a beta-lactamase promoter system, or a promoter system from phage lambda.

Other microbes, such as yeast, may also be used for expression. Saccharomyces is a preferred host, with suitable vectors having expression control sequences, such as promoters, including 3-phosphoglycerate kinase or other glycolytic enzymes, and an origin of replication, termination sequences and the like as desired.

Mammalian tissue cell culture can also be used to express and produce the antibodies of the present invention (See Winnacker, *From Genes to Clones* (VCH Publishers, N.Y., 1987). Eukaryotic cells are preferred, because a number of suitable host cell lines capable of secreting intact antibodies have been developed. Preferred suitable host cells for expressing nucleic acids encoding the immunoglobulins of the invention include: monkey kidney CV1 line transformed by SV40 (COS-7, ATCC CRL 1651); human embryonic kidney line (293) (Graham et al., 1977, *J. Gen. Virol.* 36:59); baby hamster kidney cells (BHK, ATCC CCL 10); Chinese hamster ovary-cells-DHFR (CHO, Urlaub and Chasin, 1980, *Proc. Natl. Acad. Sci. U.S.A.* 77:4216); mouse sertoli cells (TM4, Mather, 1980, *Biol. Reprod.* 23:243–251); monkey kidney cells (CV1 ATCC CCL 70); african green monkey kidney cells (VERO-76, ATCC CRL 1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); and, TRI cells (Mather et al., 1982, *Annals N.Y. Acad. Sci.* 383:44–46); baculovirus cells.

The vectors containing the polynucleotide sequences of interest (e.g., the heavy and light chain encoding sequences and expression control sequences) can be transferred into the host cell. Calcium chloride transfection is commonly utilized for prokaryotic cells, whereas calcium phosphate treatment or electroporation can be used for other cellular hosts.

(See generally Sambrook et al., *Molecular Cloning: A Laboratory Manual* (Cold Spring Harbor Press, 2nd ed., 1989) (incorporated by reference in its entirety for all purposes). When heavy and light chains are cloned on separate expression vectors, the vectors are co-transfected to obtain expression and assembly of intact immunoglobulins. After introduction of recombinant DNA, cell lines expressing immunoglobulin products are cell selected. Cell lines capable of stable expression are preferred (i.e., undiminished levels of expression after fifty passages of the cell line).

Once expressed, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (See generally Scopes, *Protein Purification* (Springer-Verlag, N.Y., 1982). Substantially pure immunoglobulins of at least about 90 to 95% homogeneity are preferred, and 98 to 99% or more homogeneity most preferred.

Frequently, the polypeptides and antibodies will be labeled by joining, either covalently or non-covalently, a substance which provides for a detectable signal. A wide variety of labels and conjugation techniques are known and are reported extensively in both the scientific and patent literature. Thus, an antibody used for detecting an analyte can be directly labeled with a detectable moiety, or may be indirectly labeled by, for example, binding to the antibody a secondary antibody that is, itself directly or indirectly labeled.

The antibodies of this invention are also used for affinity chromatography in isolating differentially expressed proteins. Columns are prepared, e.g., with the antibodies linked to a solid support, e.g., particles, such as agarose, Sephadex, or the like, where a cell lysate is passed through the column, washed, and treated with increasing concentrations of a mild denaturant, whereby purified differentially expressed polypeptides are released.

A further approach for isolating DNA sequences which encode a human monoclonal antibody or a binding fragment thereof is by screening a DNA library from human B cells according to the general protocol outlined by Huse et al, *Science* 246:1275–1281 (1989) and then cloning and amplifying the sequences which encode the antibody (or binding fragment) of the desired specificity. Such B cells can be obtained from a human immunized with the desired antigen, fragments, longer polypeptides containing the antigen or fragments or anti-idiotypic antibodies. Optionally, such B cells are obtained from an individual who has not been exposed to the antigen. B cell can also be obtained from transgenic non-human animals expressing human immunoglobulin sequences. The transgenic non-human animals can be immunized with an antigen or collection of antigens. The animals can also be unimmunized. B cell mRNA sequences encoding human antibodies are used to generate cDNA using reverse transcriptase. The V region encoding segments of the cDNA sequences are then cloned into a DNA vector that directs expression of the antibody V regions. Typically the V region sequences are specifically amplified by PCR prior to cloning. Also typically, the V region sequences are cloned into a site within the DNA vector that is constructed so that the V region is expressed as a fusion protein. Examples of such fusion proteins include m13 coliphage gene 3 and gene 8 fusion proteins. The collection of cloned V region sequences is then used to generate an expression library of antibody V regions. To generate an expression library, the DNA vector comprising the cloned V region sequences is used to transform eukaryotic or prokaryotic host cells. In addition to V regions, the vector can optionally encode all or part of a viral genome, and can comprise viral packaging sequences. In some cases the vector does not comprise an entire virus genome, and the vector is then used together with a helper virus or helper virus DNA sequences. The expressed antibody V regions are found in, or on the surface of, transformed cells or virus particles from the transformed cells. This expression library, comprising the cells or virus particles, is then used to identify V region sequences that encode antibodies, or antibody fragments reactive with predetermined antigens. To identify these V region sequences, the expression library is screened or selected for reactivity of the expressed V regions with the predetermined antigens. The cells or virus particles comprising the cloned V region sequences, and having the expressed V regions, are screened or selected by a method that identifies or enriches for cells or virus particles that have V regions reactive (e.g., binding association or catalytic activity) with a predetermined antigen. For example, radioactive or fluorescent labeled antigen that then binds to expressed V regions can be detected and used to identify or sort cells or virus particles. Antigen bound to a solid matrix or bead can also be used to select cells or virus particles having reactive V regions on the surface. The V region sequences thus identified from the expression library can then be used to direct expression, in a transformed host cell, of an antibody or fragment thereof, having reactivity with the predetermined antigen.

The protocol described by Huse is rendered more efficient in combination with phage-display technology. See, e.g., Dower et al., WO 91/17271 and McCafferty et al., WO 92/01047, U.S. Pat. Nos. 5,871,907, 5,858,657, 5,837,242, 5,733,743 and 5,565,332 (each of which is incorporated by reference in its entirety for all purposes). In these methods, libraries of phage are produced in which members (display packages) display different antibodies on their outer surfaces. Antibodies are usually displayed as Fv or Fab fragments. Phage displaying antibodies with a desired specificity can be selected by affinity enrichment to the antigen or fragment thereof. Phage display combined with immunized transgenic non-human animals expressing human immunoglobulin genes can be used to obtain antigen specific antibodies even when the immune response to the antigen is weak.

In a variation of the phage-display method, human antibodies having the binding specificity of a selected murine antibody can be produced. See, for example, Winter, WO 92/20791. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding (e.g., at least $10^8$ and preferably at least $10^9$ $M^{-1}$) can then be selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for the selected are selected. Artificial antibodies that are similar to human antibodies can be obtained from phage display libraries that incorporate random or synthetic sequences, for example, in CDR regions.

In another embodiment of the invention, fragments of antibodies against differentially expressed protein or protein analogs are provided. Typically, these fragments exhibit specific binding to the differentially expressed protein receptor similar to that of a complete immunoglobulin. Antibody fragments include separate heavy chains, light chains $F_{ab}$, $F_{ab}'$ $F_{(ab')2}$ and $F_v$. Fragments are produced by recombinant DNA techniques, or by enzymic or chemical separation of intact immunoglobulins.

The antibodies can be monovalent antibodies. Methods for preparing monovalent antibodies are well known in the art. For example, one method involves recombinant expression of immunoglobulin light chain and modified heavy chain. The heavy chain is truncated generally at any point in the $F_c$ region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, $F_{ab}$ fragments, can be accomplished using routine techniques known in the art.

An alternative approach is the generation of humanized immunoglobulins by linking the CDR regions of non-human antibodies to human constant regions by recombinant DNA techniques. See U.S. Pat. No. 5,585,089 (Queen et al.). Humanized forms of non-human (e.g., murine) antibodies are immunoglobulins, immunoglobulin chains or fragments thereof (such as $F_v$, $F_{ab}$, $F_{ab'}$, $F_{ab2}$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an $F_c$ region, typically that of a human immunoglobulin (Jones et al., *Nature* (1986) 321:522–525; Riechmann et al, *Nature* (1988) 332:323–329; and Presta, *Curr. Op. Struct. Biol.* (1992) 2: 593–596).

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments, such as $IgG_1$ and $IgG_4$. Human isotype $IgG_1$ is preferred. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody (referred to as the donor immunoglobulin). See, Queen et al., 1989, *Proc. Natl. Acad. Sci. U.S.A.* 86:10029–10033 and WO 90/07861, U.S. Pat. No. 5,693,762, U.S. 5,693,761, U.S. 5,585,089, U.S. 5,530,101 and Winter, U.S. Pat. No. 5,225,539 (incorporated by reference in their entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid should usually be substituted by the equivalent framework amino acid from the mouse antibody when it is reasonably expected that the amino acid: (1) noncovalently binds antigen directly, (2) is adjacent to a CDR region, (3) otherwise interacts with a CDR region (e.g. is within about 6 A of a CDR region), or (4) participates in the VL-VH interface.

Other candidates for substitution are acceptor human framework amino acids that are unusual for a human immunoglobulin at that position. These amino acids can be substituted with amino acids from the equivalent position of the mouse donor antibody or from the equivalent positions of more typical human immunoglobulins. Other candidates for substitution are acceptor human framework amino acids that are unusual for a human immunoglobulin at that position. The variable region frameworks of humanized immunoglobulins usually show at least 85% sequence identity to a human variable region framework sequence or consensus of such sequences.

Human antibodies can also be produced using various techniques known in the art, including phage display libraries discussed above (Hoogenboom and Winter, *J. Mol. Biol.* (1991) 227: 381; Marks et al., *J. Mol. Biol.* (1991) 222: 581). The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.* (1991) 147(1): 86–95). Similarly, human antibodies can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016; see also Marks et al., *Bio/Technology* 10, 779–783 (1992); Lonberg et al., *Nature* (1994) 368: 856–859; Morrison, *Nature* (1994) 368: 812–13; Fishwild et al., *Nature Biotechnology* (1996) 14: 845–51; Neuberger, *Nature Biotechnology* (1996) 14: 826; Lonberg and Huszar, *Intern. Rev. Immunol.* (1995) 13: 65–93.

Bispecific antibodies are monoclonal, preferably human or humanized, antibodies that have binding specificities for at least two different antigens. In the present case, one of the binding specificities is for the differentially expressed protein, the other one is for any other antigen, and preferably for a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities Milstein and Cuello, *Nature* (1983) 305: 537–539). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.* (1991) 10:3655–3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology* (1986) 121:210.

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-differentially expressed protein antibodies of the invention have various utilities. For example, anti-differentially expressed protein antibodies can be used in diagnostic assays for a differentially expressed protein, e.g., detecting its expression in specific cells, tissues, or serum. Various diagnostic assay techniques can be used, such as competitive binding assays, direct or indirect sandwich assays and immunoprecipitation assays conducted in either heterogeneous or homogeneous phases (Zola, *Monoclonal Antibodies: A Manual of Techniques*, CRC Press, Inc. (1987) pp. 147–158). The antibodies used in the diagnostic assays can be labeled with a detectable moiety. The detectable moiety should be capable of producing, either directly or indirectly, a detectable signal. For example, the detectable moiety can be a radioisotope, such as 3H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety can be employed, including those methods described by Hunter et al., *Nature* (1962) 144: 945; David et al., *Biochemistry* (1974) 13:1014; Pain et al., *J. Immunol. Meth.* (1981) 40:219; and Nygren, *J. Histochem. and Cytochem.* (1982) 30:407.

Anti-differentially expressed protein antibodies also are useful for the affinity purification of differentially expressed protein from recombinant cell culture or natural sources. In this process, the antibodies against differentially expressed protein are immobilized on a suitable support, such a Sephadex resin or filter paper, using methods well known in the art. The immobilized antibody then is contacted with a sample containing the differentially expressed protein to be purified, and thereafter the support is washed with a suitable solvent that will remove substantially all the material in the sample except the differentially expressed protein, which is bound to the immobilized antibody. Finally, the support is washed with another suitable solvent that will release the differentially expressed protein from the antibody.

14. Pharmaceutical Compositions and Methods of Administration

The anti-differentially expressed protein antibodies can also be used in treatment. In some methods, the genes encoding the antibodies are provided, such that the antibodies bind to and modulate the differentially expressed protein within the cell. In other methods, a therapeutically effective amount of a differentially expressed protein, agonist or antagonist is administered to a patient. A "therapeutically effective amount", "pharmacologically acceptable dose", "pharmacologically acceptable amount" means that a sufficient amount of an immunosuppressive agent or combination of agents is present to achieve a desired result, e.g., preventing, delaying, inhibiting or reversing a symptom of a disease or disorder or the progression of disease or disorder when administered in an appropriate regime.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed., 1989). The pharmaceutical compositions of the present invention generally comprise a differentially expressed protein, agonist or antagonist in a form suitable for administration to a patient. The pharmaceutical compositions are generally formulated as sterile, substantially isotonic and in full compliance with all Good Manufacturing Practice (GMP) regulations of the U.S. Food and Drug Administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, carriers known in the art.

In some preferred methods, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, flmaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Suitable formulations for rectal administration include, for example, suppositories, which consist of the packaged nucleic acid with a suppository base. Suitable suppository bases include natural or synthetic triglycerides or paraffin hydrocarbons. In addition, it is also possible to use gelatin rectal capsules which consist of a combination of the packaged nucleic acid with a base, including, for example, liquid triglycerides, polyethylene glycols, and paraffin hydrocarbons.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and nonaqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. Formulations for injection can be presented in unit dosage form, e.g., in ampules or in multidose containers, with an added preservative. The compositions are formulated as sterile, substantially isotonic and in fall compliance with all Good Manufacturing Practice (GMP) regulations of the U.S. Food and Drug Administration.

Injection solutions and suspensions can be prepared from sterile powders, granules, and tablets of the kind previously described. Cells transduced by the packaged nucleic acid as described above in the context of ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions resulting from expression of the differentially expressed proteins of the invention, the physician evaluates circulating plasma levels of the vector, vector toxicities, progression of the disease, and the production of anti-vector antibodies. In general, the dose equivalent of a naked nucleic acid from a vector is from about 1 $\mu$g to 100 $\mu$g for a typical 70 kilogram patient, and doses of vectors which include a retroviral particle are calculated to yield an equivalent amount of therapeutic nucleic acid.

For administration, inhibitors and transduced cells of the present invention can be administered at a rate determined by the $LD_{50}$ of the inhibitor, vector, or transduced cell type, and the side-effects of the inhibitor, vector or cell type at various concentrations, as applied to the mass and overall health of the patient. Administration can be accomplished via single or divided doses.

Transduced cells are prepared for reinfusion according to established methods (see Abrahamsen et al., *J. Clin. Apheresis* 6:48–53 (1991); Carter et al., *J. Clin. Arpheresis* 4:113–117 (1998); Aebersold etal., *J. Immunol. Meth.* 112:1–7 (1998); Muul et al., *J. Immunol. Methods* 101:171–181 (1987); and Carter et al., *Transfusion* 27:362–365 (1987)). After a period of about 2–4 weeks in culture, the cells should number between $1 \times 10^8$ and $1 \times 10^{12}$. In this regard, the growth characteristics of cells vary from patient to patient and from cell type to cell type. About 72 hours prior to reinfusion of the transduced cells, an aliquot is taken for analysis of phenotype, and percentage of cells expressing the therapeutic agent.

15. Kits

The differentially expressed protein, agonist or antagonist of the present invention or their homologs are useful tools for examining expression and regulation of S1o family potassium channels. Reagents that specifically hybridize to nucleic acids encoding differentially expressed proteins of the invention (including probes and primers of the differentially expressed proteins), and reagents that specifically bind to the differentially expressed proteins, e.g., antibodies, are used to examine expression and regulation.

Nucleic acid assays for the presence of differentially expressed proteins in a sample include numerous techniques are known to those skilled in the art, such as Southern analysis, northern analysis, dot blots, RNase protection, S1 analysis, amplification techniques such as PCR and LCR, high density oligonucleotide array analysis, and in situ hybridization. In in situ hybridization, for example, the target nucleic acid is liberated from its cellular surroundings in such as to be available for hybridization within the cell while preserving the cellular morphology for subsequent interpretation and analysis. The following articles provide an overview of the art of in situ hybridization: Singer et al., *Biotechniques* 4:230–250 (1986); Haase et al., *Methods in Virology*, vol. VII, pp. 189–226 (1984); and *Nucleic Acid Hybridization: A Practical Approach* (Hamnes et al., eds. 1987). In addition, a differentially expressed protein can be detected with the various immunoassay techniques described above. The test sample is typically compared to both a positive control (e.g., a sample expressing recombinant differentially expressed protein) and a negative control.

The present invention also provides for kits for screening B cell activity modulators. Such kits can be prepared from readily available materials and reagents. For example, such kits can comprise any one or more of the following materials: the differentially expressed proteins, agonists, or antagonists of the present invention, reaction tubes, and instructions for testing the activities of differentially expressed genes. A wide variety of kits and components can be prepared according to the present invention, depending upon the intended user of the kit and the particular needs of the user. For example, the kit can be tailored for in vitro or in vivo assays for measuring the activity of a differentially expressed proteins or B cell activity modulators of the present invention.

The invention further provides kits comprising probe arrays as described above. Optional additional components of the kit include, for example, other restriction enzymes, reverse-transcriptase or polymerase, the substrate nucleoside triphosphates, means used to label (for example, an avidin-enzyme conjugate and enzyme substrate and chromogen if the label is biotin), and the appropriate buffers for reverse transcription, PCR, or hybridization reactions.

Usually, the kits of the present invention also contain instructions for carrying out the methods.

EXAMPLES

Methods

B Cell Purification and Stimulation

Splenic B cells from non-transgenic, $Ig^{HEL}$ or sHEL/$Ig^{HEL}$ transgenic mice were purified at room temperature in 1% bovine calf serum in RPMI. The spleen cells were stained with CD4, CD8 and Mac-1 FITC conjugated antibodies (Caltag) and depleted of T cells and macrophages with sheep anti-FITC magnetic beads (Perseptive Biosystems). The remaining cells were 85–95% B220 positive and were either lysed immediately (naive and tolerant cell preps) or stimulated in RPMI with 1% serum at 37° C. at 2–3×10$^6$ cells/ml. For stimulation experiments, HEL (Sigma) was used at 500 ng/ml, goat anti-mu (Jackson Labs) at 10 μg/ml, FK506 at 10 ng/ml, PD98059 (NEB) at 20 μM unless stated otherwise, ionomycin at 1 μM and EGTA at 3 mM. Cells were preincubated for 45 minutes with PD98059, 15 minutes with FK506 and 2 minutes with EGTA before addition of HEL or anti-mu. Mock stimulations were performed by addition of carrier alone for stimuli or inhibitors. At the end of the incubation, the cells were pelleted by centrifugation, resuspended in a minimal volume of medium (about 50 μl) by pipetting and lysed in 0.5–1 ml Trizol (Gibco BRL).

Naïve and tolerant B cells were also purified by FACS. Spleen cells from $Ig^{HEL}$ and sHEL/$Ig^{HEL}$ mice were stained for B220 and CD21 and sorted for B220 positive, $CD21^{medium}$ cells. Marginal zone cells (CD21 high) were excluded from the gate. FACS allowed us to control for the fact that B cells in sHEL/$Ig^{HEL}$ mice are generally present at lower numbers than $Ig^{HEL}$ mice and the marginal zone B cell subset is absent. Thus, expression changes between anergic and naive cells determined from samples purified by negative depletion that are also seen in cells purified by FACS are unlikely to be due to systematic differences in the amount of marginal zone B cells or non-B cells in the two samples.

RNA Purification, CDNA Synthesis, In Vitro Transcription (IVT) and Array Hybridization Trizol lysates were phenol-extracted and precipitated with isopropanol. Poly A+ RNA was purified with Oligotex (Qiagen). cDNA was synthesised with a SuperscriptII cDNA synthesis kit (Gibco BRL) using a T7:(dT)24 oligo to prime the first strand and purified by phenol extraction and ethanol precipitation. The cDNA was used as a template for in vitro transcription (IVT) using the Megascript system (Ambion) with the inclusion of biotinylated CTP and UTP. The IVT product was separated from unincorporated nucleotides using a RNeasy column (Qiagen) and was fragmented with 150 mM magnesium chloride at 95° C. Fragmented cRNA was hybridised in a volume of 200 μl 1 M sodium chloride, 10 mM Tris pH 7.4, 0.005% Triton X100 including 1 mg/ml BSA, 0.1 mg/ml herring sperm DNA and bacterial transcripts spiked at known concentrations. Hybridization was for 12–16 hours at 40° C. with rotation. The arrays were incubated at 50° C. for 1 hr then washed to 0.5×SSPE, room temperature. Biotinylated hybridised cRNA was developed by staining with strepavidin-PE and the chips were scanned with a Molecular Dynamics scanner (see also Lipshutz, R. J. et al., *Nat. Genet* (1999) 21: 20–4; this reference and references cited therein are herein incorporated by reference).

Statistical Analysis and Querying

Each gene on the arrays was tiled as a collection of approximately 20 probe pairs. Each probe pair contains a 25 mer oligo that is exactly complementary to the transcript (the perfect match oligo) and a second oligo that contains a single base mismatch at the middle base. The perfect match—mismatch intensities (PM—MM) were calculated for each probe pair for each gene in each experiment. For each probe pair, the PM—MM values were compared by t test between the two conditions (e.g. resting vs stimulated, matched t test; naive vs anergic, unmatched t test). Positive t values associated with a probability of less than 0.1 were scored as increased, negative t values with a probability of less than 0.1 were scored as decreased. The number of increased and decreased probe pairs associated with each gene was determined and called npos and nneg respectively (of the approximately 20 probe pairs tiled for each gene). The distribution of npos and nneg is binomial where p=0.1 and n=number of probe pairs for that gene. The probability of scoring npos or more of the total number of probe pairs was determined. The same analysis was done for decreased genes using nneg. A probability value was chosen so that the probability of one or more false positive in any query was less than 5% after correcting for the number of genes queried. For example, 280 genes had a median fold change after 1 hour activation of 1.75 or greater. The adjusted 5% probability for 280 trials is 0.00018, and 59 of the 280 changes were significant at this level. We also analysed our data using an analysis of variance approach where the variation in PM—MM values for each gene was partitioned into that due to error (within group), probe pair, or the experimental factor (e.g. resting vs stimulated). The results were broadly the same as for the t test strategy described above. However, the t test strategy is more robust to rare probes that had very high and anomalous signals.

To analyse the 6 hr timepoint (2 experiments) and the sorted naive and tolerant B cells we used the following query. For a given transcript, each probe pair was scored as increased in sample A relative to sample B if $(PM-MM)_A-(PM-MM)_B>30$ and $(PM-MM)_A>1.3\times(PM-MM)_B$ and decreased by the reverse. A transcript was scored as increased in each pairwise comparison if the number of increased probe pairs was 3 or greater, the ratio of increased to decreased probe pairs was greater than 3 and the ratio of average difference intensities was greater than 1.8. Decreased genes were determined by the reverse of this algorithm. Based on comparisons of all genes between closely matched samples the false positive rate of this query was empirically determined to be approximately 1 in 18 transcripts in any pairwise comparison. Consistent changes across the 2 experiments have a false positive rate of approximately 1 in 300.

Measurement of Gene Expression

An intensity for each gene was calculated based on a trimmed mean of the PM—MM values. Values less than 5 were considered indistinguishable and were set to 5. The resulting average difference intensities were used to represent expression levels in the figures and to calculate fold changes.

Results

To identify molecular events distinguishing activation and tolerance in peripheral lymphocytes, gene expression profiles were analyzed in lymphocytes undergoing these opposing processes that were in all other respects as closely matched as possible. Homogeneous populations of B lymphocytes specific for a well defined antigen, hen egg lysozyme (HEL), were obtained from the spleen of mice transgenic for a B cell antigen receptor against HEL ($Ig^{HEL}$ mice). Resting B cells from $Ig^{HEL}$ mice are antigenically naive and in G0 of cell cycle. Acute stimulation with foreign HEL triggers their activation and entry into G1, promoting clonal proliferation and antibody secretion provided that T cells or bacterial lipopolysaccharides are present as costimuli. In parallel, homogeneous populations of self-tolerant (anergic) B cells were obtained from the spleen of double transgenic mice which carry the same $Ig^{HEL}$ receptor transgene but also express HEL as a self antigen (sHEL:$Ig^{HEL}$ mice). Despite expressing the same HEL-specific receptors and being matched for stage of development, the tolerant cells are unable to make a proliferative or antibody response to HEL. Instead, repeated stimulation of their receptors by self HEL causes them to make responses that actively reinforce tolerance, such as altered migration, Fas-dependent and Fas-independent apoptosis, and inhibition of plasma cell differentiation. Peripheral tolerant B cells in the sHEL:$Ig^{HEL}$ mice first encountered antigen during development in the bone marrow and have a life span of about 2 weeks. Despite the fact that these cells have been exposed to self-antigen for differing lengths of time, they appear homogenous with respect to the aspects of tolerance listed above, and as measured by continuous calcium oscillations and uniformly low expression of the activation markers B7-2 and CD69. "Differential expression," or grammatical equivalents as used herein, refers to both qualitative as well as quantitative differences in the genes' temporal and/or cellular expression patterns within and among B cells. Thus, a differentially expressed gene can qualitatively have its expression altered, including an activation or inactivation in, for example, tolerant versus immunosuppressed cells, rested, naive or activated cells, or in a healthy B cell response versus an abnormal B cell response. Genes can be turned on or turned off in a particular state, relative to another state. Any comparison of two or more states can be made. Such a qualitatively regulated gene will exhibit an expression pattern within a state or cell type which can be detectable by standard techniques in one such state or cell type, but can be not detectable in both. Alternatively, the determination can be quantitative in that expression is increased or decreased; that is, the expression of the gene is either upregulated, resulting in an increased amount of transcript, or downregulated, resulting in a decreased amount of transcript. The degree to which expression differs need only be large enough to quantify using standard characterization techniques, for example, by using Affymetrix GENECHIP™ expression arrays (Lockhart, *Nature Biotechnology*, (1996) 14:1675–1680; this reference and all references cited therein are incorporated by reference). Other methods include, but are not limited to, quantitative reverse transcriptase PCR, Northern analysis and RNase protection. Preferably the change or modulation in expression (i.e., upregulation or dowuregulation) is at least about 5%, more preferably at least about 10%, more preferably, at least about 20%, more preferably, at least about 30%, or more preferably by at least about 50%, or at least about 75%, and more preferably at least about 90%.

A relatively small set of response genes was associated with the initial phase of B lymphocyte activation, one hour after foreign antigen stimulation ex vivo (FIG. 1). Of the 6,500 genes screened in seven independent replicate experiments, mRNAs for only thirty seven were significantly increased and twenty two were decreased (FIG. 1, p<0.00018). A large fraction of the increased and decreased transcripts encode transcriptional regulators. While a small number of these 59 transcripts have been previously identified as early response genes in B cells, validating the data obtained here, most were not previously known to participate in B cell responses. Many of these genes encode proteins with established roles in mitotic and anti-apoptotic responses by lymphocytes or other cell types. For example, LSIRF is necessary for mitogenesis as B cells from mice deficient in this gene are unable to proliferate in response to anti-IgM. Furthermore, expression of A1, a bcl-2 homologue, can be sufficient to prevent apoptosis after antigen receptor engagement on B cells. Conversely, downregulation of LKLF can be obligatory for B cell activation as T cells deficient in LKLF have a spontaneously activated cell surface phenotype. Finally, c-myc, c-fos, and FosB are associated with mitogenesis through their status as oncogenes and Egr-1 and Egr-2 have been specifically implicated in B cell mitogenesis.

The pattern of gene expression was much more extensively altered after six hours of antigen stimulation. While mRNAs for many of the 1 hr induced genes had decreased by this time (e.g., Egr-1, PAC-1, c-fos, FosB in FIG. 1C), others in the early response set showed sustained or exaggerated responses at 6 hours (e.g., A1 and MIP-1a/b in FIG. 1C, LKLF and GILZ in FIG. 1D). Many of the additional gene expression changes are consistent with movement to the G1 phase of the cell cycle, including upregulation of CDK4 and cyclin D2.

The same set of 6,500 genes was screened for expression changes in anergic B cells undergoing peripheral tolerance responses to HEL antigen in vivo. Expression was compared between five tolerant B cell preparations from sHEL:$Ig^{HEL}$ mice and four naive B cell preparations from $Ig^{HEL}$ mice, where paired samples were purified by negative selection with magnetic beads. A further two preparations each of tolerant and naive B cells were purified by positive selection on a fluoresence activated cell sorter (FACS). Using an algorithm that requires consistency between both purification methods, expression of only twenty genes was significantly increased and eight genes decreased in tolerant cells (FIG. 2, $p<0.00034$). One of these changes can be due to contaminating erythroid cells (carbonic anhydrase II) because this mRNA species was much less abundant in FACS-sorted B cells.

To determine the extent of overlap between the responses to the same antigen when presented as self or foreign the data was compared using both stringent (p value corrected for number of trials) and non-stringent (uncorrected) queries. Of the 19 genes upregulated by self-antigen (excluding carbonic anhydrase II), 7 were also upregulated by foreign antigen after 1 hour ($p<0.00018$) or 6 hours (2 of 2 experiments): NAB2 and neurogranin were comparably upregulated by both forms of antigen; Egr-1, Egr-2, Gfi-1, cyclin D2 and Cctq were upregulated to a greater extent by foreign antigen than by self-antigen. Of the remaining 12 transcripts upregulated in tolerant cells, there was weaker evidence for upregulation of 4 genes after 6 hours exposure to foreign antigen (SATB1, CD83, TGIF and CD72, 1 of 2 experiments). For 8 of the 19 transcripts upregulated by self-antigen, there was no evidence for upregulation by foreign antigen. Seven of 8 transcripts downregulated by self-antigen were downregulated by 6 hours exposure to foreign antigen in 2 of 2 experiments (4 transcripts) or 1 of 2 experiments (3 transcripts). In summary, most, but not all, of the transcript changes induced by selfantigen were also regulated by foreign antigen, though to differing degrees.

Only 16 of more than 500 transcript changes caused by foreign antigen were also regulated by self-antigen ($p<0.05$, fold change>1.8, at least 1 of 2 experiments with sorted cells): nearly all of the response to foreign antigen is blocked in tolerant cells. The response to foreign antigen is measured after in vitro stimulation whereas the response to self-antigen occurs in vivo. This was necessary because of technical limitations on the length of time required to isolate and purify activated cells after stimulation in vivo relative to the time of activation. However, an analysis of transcript changes caused by in vitro incubation in the absence of antigen is not consistent with this causing a partial activation response: in fact, some of the genes that were upregulated by antigen are downregulated by in vitro incubation and vice vers. Therefore, the differences that described between exposure to self and foreign antigen can reflect biological differences between tolerance and immunity rather than an "adjuvant" effect of in vitro incubation.

FK506, a commonly used immunosuppressant drug, can block B cell activation and can be a phenocopy of tolerance. B cells were stimulated as for FIG. 1 but in the presence of 10 ng/ml FK506. This concentration was chosen as it is within the range maintained in the blood of kidney and liver transplant patients receiving FK506 (also called Tacrolimus and Prograf. Of the 59 genes defined previously as increasing or decreasing 1 hr after B lymphocyte activation, only one third of these were efficiently suppressed by this dose of FK506 (FIG. 3). Some early response genes (for example, gadd 153) were superinduced in the presence of drug. By this analysis, the suppressive effects of FK506 on lymphocyte activation are much more limited than the suppression achieved by peripheral tolerance. The response genes blocked by the drug include genes that are triggered by self-antigen, such as Egr-2 and CD72, which can contribute to the active maintenance of tolerance. Cells stimulated in the presence of FK506 do not activate NFAT, NFkB nor JNK though signaling through Erk is intact. Self-antigen causes apparent activation of more signaling pathways, as signaling through both Erk and NFAT is intact, but the response to antigen measured by transcript profiling is much more repressed than is achieved by FK506.

Naïve cells were stimulated in the presence of EGTA. This reagent had essentially the same effect on the transcript profile as FK506 (FIG. 3C), confirming that FK506 affected transcript levels through a calcium/calcineurin-dependent pathway. A notable exception to this was MyD 116. Antigen induced upregulation of this transcript was repressed by FK506 (n=5) but not by EGTA (n=2), which can be indicative of secondary effects of the drug other than calcineurin inhibition. However, there were no FK506-induced changes in transcripts other than those altered in the antigen activation response.

Figures 4A, 4B:
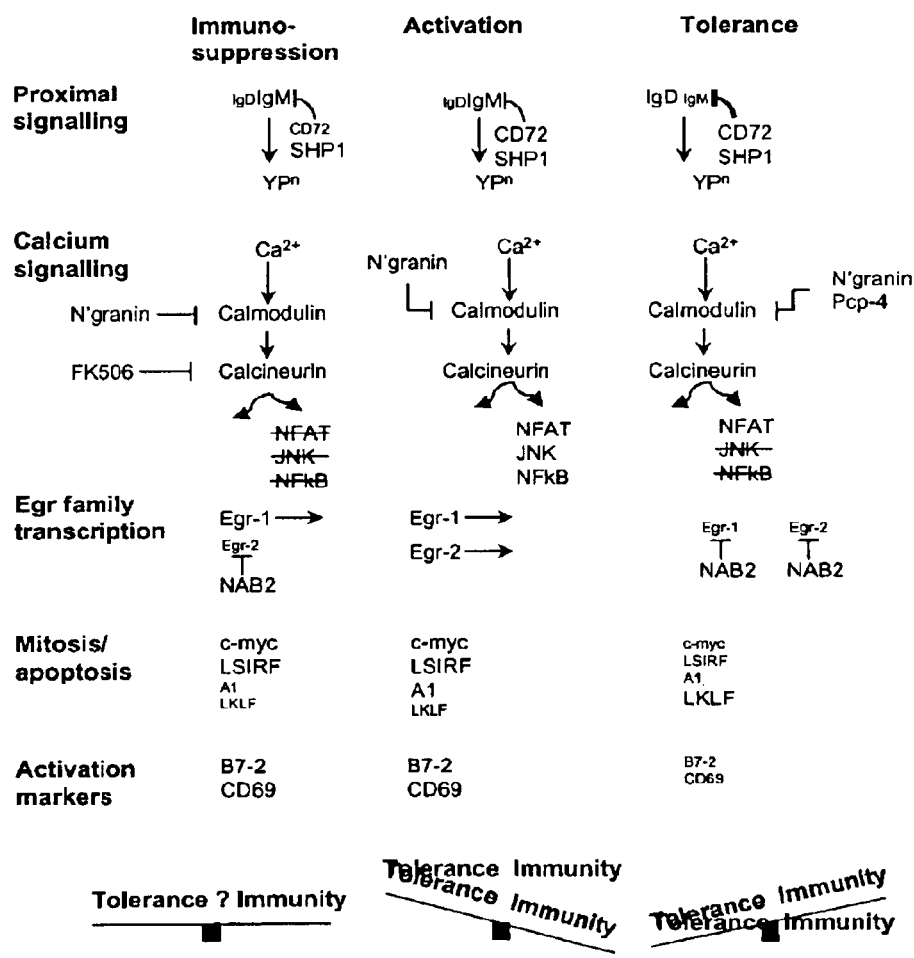
FIGS. 4A and 4B.

The effects of tolerance and pharmacological reagents on B cell activation can be used to assign transcriptional events downstream of particular signaling pathways (FIG. 4A). Transcriptional events that are suppressed by FK506 and EGTA after antigen stimulation of naive cells can be firmly assigned to be downsteam of the calcium/calcineurin pathway. These can be further subdivided on the basis of their expression levels in tolerant cells. In these cells, self-antigen evokes chronic low calcium oscillations that are sufficient to induce nuclear translocation of NFAT but not to activate NFkB nor JNK, though all three pathways are dependent on calcium/calcineurin. Thus, FK506-sensitive upregulation of genes not altered in tolerant cells is suggestive of signaling through NFkB or JNK, whereas FK506-sensitive genes that are also upregulated in tolerance would be expected to be downstream of NFAT (for example, Egr-2 and CD72). Upregulation of Al is FK506 sensitive but blocked in tolerance.

In addition to NFAT, the ERK pathway is also activated in foreign or self antigen-stimulated cells. To determine downstream transcriptional effects of ERK, the effect of MEK, an ERK kinase, on B cell activation was determined. The MEK inhibitor PD98059 was titrated in B cell activation experiments and gene expression was monitored using one of the four arrays in the set (approximately 1600 genes). Upregulation of Egr-1 was totally inhibited by 20 $\mu$M PD98059 and was 50% inhibited at 5–10 $\mu$M, consistent with the potency of PD98059 against recombinant MEK (FIG. 3D). Regulation of other early response genes was less sensitive than Egr-1. Induction of three transcripts (Egr-1, NAB2 and Gfi-1) that are upregulated by both self and foreign antigen was sensitive to PD98059 (FIG. 3D) but insensitive to FK506 (FIG. 3A). Continuous activation of the ERK pathway by self-antigen can have transcriptional consequences which are distinct from those downstream of NFAT (FIG. 4A).

The strategy followed here, statistically comparing the expression of large numbers of genes in replicate cell samples that were closely matched to eliminate secondary effects, provides the first molecular picture of how self-tolerance prevents lymphocyte mitogenesis (FIG. 4B). Given the continuous signaling through the ERK and NFAT pathways in response to self antigen, it is remarkable how few of the mitogenic response genes are triggered. The loss of a mitotic response to antigen in tolerant cells is explained by the failure to upregulate LSIRF, a B cell myeloma protooncogene that is an essential transcription factor for B cell mitogenic responses, and failure to upregulate A1, an anti-apoptotic protein that is sufficient and apparently necessary to block apoptotic responses to antigen in B cells. The block to induction of the B cell lymphoma protooncogene, c-myc, is also likely to contribute since increased expression of c-myc is sufficient to promote B cell blastogenesis in transgenic mice. By comparison, it is surprising how little of the early mitogenic response is suppressed by FK506 given its ability to block foreign-antigen stimulated NFAT, NFkB and JNK. Inhibition of AI by FK506 can alone be sufficient to explain the anti-mitogenic effects of FK506, since activation in the presence of FK506 is associated with increased B cell death.

The small number of foreign-response genes that are still triggered in the tolerance response can be inhibited or subverted from pro-mitogenic roles by other gene products in the tolerant cells. The Egr-1 and Egr-2 transcription factors have been specifically implicated in B cell mitogenesis, but are induced at lower levels in tolerant cells than after activation (FIG. 2B), a quantitative difference also true for Egr-1 protein. Their mitogenic activity in tolerant cells is likely to be repressed by relatively high expression of NAB2, an Egr family inhibitor, and it Egr/NAB2 heterodimers can activate tolerance-specific genes. Inhibition by FK506 of Egr-2, and other shared activation/tolerance response genes such as CD72, shows that this immunosuppressive drug can also interfere with components of the active self-tolerance response. This effect can further limit its efficacy in establishing or restoring tolerance in autoimmunity and transplantation.

Many of the genes associated with the tolerance response can be predicted to have negative regulatory functions for maintaining the tolerant state. The function of these genes in this context is unknown but clues can be found in previous work. The largest change is an increase in mRNA from Aeg-2 (also called CRISP-3), a gene known to be controlled by Oct-2 in B cells which encodes a secreted protein of unknown function. Two others, neurogranin and pcp-4, encode related gene products that have been implicated in regulation of calcium signaling through calmodulin and they can have a role in regulation of the downstream effects caused by low level calcium spiking in tolerant cells (FIG. 4B). Two cell surface proteins upregulated in tolerant cells regulate proximal signaling pathways necessary for the maintenance of tolerance. IgD is the primary receptor isotype expressed on tolerant B cells, through which repeated binding of self antigen can trigger calcium oscillations. Proximal signaling can be decreased relative to naive cells by increased levels of CD72, which has been shown to recruit the inhibitory tyrosine phosphatase, SHP-1, and diminish BCR signaling (FIG. 4B). Increased IgD and CD72 in tolerant cells have been confirmed at the protein level.

The molecular definition of lymphocyte activation, tolerance, and FK506-immunosuppression established here can provide a guide to search for more efficient immunosuppressive drugs. In particular, the unique transcript signature associated with self-reactive cells can be used as a surrogate marker for tolerance, the phenotypes of which are not easily assayed in a high throughput way. Recent advances in high throughput screening techniques allow monitoring of gene expression after treatment of cells with a chemical library of potential drug leads. By defining a molecular signature for peripheral tolerance, screens for new drugs that better mimic the tolerance phenotype can be screened. With this approach, the drug target need not be known and need not be represented in the original expression screening platform, nor does the level of transcript for the target protein itself need to change. To develop drugs that better emulate the active process of peripheral tolerance, the desired small molecule would suppress members of the activation-only early response gene subset defined here, while leaving unaffected the subset of early response genes that also participate in tolerance. A drug with this profile could likely to block immunity but not tolerance, which can be key to (re)establishing immunological unresponsiveness in autoimmunity, allergy, or tranplantation.

REFERENCES

1. Goodnow, C. C. et al. Self-tolerance checkpoints in B lymphocyte development. *Adv Immunol* 59, 279–368 (1995).

2. Liu, J. et aL Calcineurin is a common target of cyclophilin-cyclosporin A and FKBP-FK506 complexes. *Cell* 66, 807–15 (1991).

3. Kino, T. et al. FK-506, a novel immunosuppressant isolated from a Streptomyces. I. Fermentation, isolation, and physico-chemical and biological characteristics. *J Antibiot* (Tokyo) 40, 1249–55 (1987).

4. Borel, J. F., Feurer, C., Gubler, H. U. & Stahelin, H. Biological effects of cyclosporin A: a new antilymphocytic agent. *Agents Actions* 6, 468–75 (1976).

5. Wicker, L. S. et al. Suppression of B cell activation by cyclosporin A, FK506 and rapamycin. *Eur J Immunol* 20, 2277–83 (1990).

6. Cooke, M. P. et aL Immunoglobulin signal transduction guides the specificity of B cell-T cell interactions and is blocked in tolerant self-reactive B cells. *J Exp Med* 179, 425–38 (1994).

7. Healy, J. 1. et al. Different nuclear signals are activated by the B cell receptor during positive versus negative signaling. *Immunity* 6, 419–28 (1997).

8. Rathmell, J. C., Fournier, S., Weintraub, B. C., Allison, J. P. & Goodnow, C. C. Repression of B7.2 on self-reactive B cells is essential to prevent proliferation and allow Fas-mediated deletion by CD4(+) T cells. *J Exp Med* 188, 651–9 (1998).

9. Lipshutz, R. J., Fodor, S. P., Gingeras, T. R. & Lockhart, D. J. High density synthetic oligonucleotide arrays. *Nat Genet* 21, 20–4 (1999).

10. Seyfert, V. L., Sukhatme, V. P. & Monroe, J. G. Differential expression of a zinc finger-encoding gene in response to positive versus negative signaling through receptor immunoglobulin in murine B lymphocytes. *Mol Cell Biol* 9, 2083–8 (1989).

11. Newton, J. S. et al. B cell early response gene expression coupled to B cell receptor, CD40 and interleukin-4 receptor co-stimulation: evidence for a role of the Egr-2/krox 20 transcription factor in B cell proliferation. *Eur J Immunol* 26, 811–6 (1996).

12. Monroe, J. G. Up-regulation of c-fos expression is a component of the mlg signal transduction mechanism but is not indicative of competence for proliferation. *J Immunol* 140, 1454–60 (1988).

13. Huo, L. & Rothstein, T. L. Receptor-specific induction of individual AP-1 components in B lymphocytes. *J Immunol* 154, 3300–9 (1995).

14. Grumont, R. J., Rasko, J. E., Strasser, A. & Gerondakis, S. Activation of the mitogen-activated protein kinase pathway induces transcription of the PAC-1 phosphatase gene. *Mol Cell Biol* 16, 2913–21 (1996).

15. Mittelstadt, P. R. & DeFranco, A. L. Induction of early response genes by cross-linking membrane Ig on B lymphocytes. *J Immunol* 150, 4822–32 (1993).

16. Hong, J. X., Wilson, G. L., Fox, C. H. & Kehrl, J. H. Isolation and characterization of a novel B cell activation gene. *J Immunol* 150, 3895–904 (1993).

17. Mittrucker, H. W. et al. Requirement for the transcription factor LSIRF/IRF4 for mature B and T lymphocyte function. *Science* 275, 540–3 (1997).

18. Grumont, R. J., Rourke, I. J. & Gerondakis, S. Rel-dependent induction of A1 transcription is required to protect B cells from antigen receptor ligationinduced apoptosis. *Genes Dev* 13, 400–11 (1999).

19. Kuo, C. T., Veselits, M. L. & Leiden, J. M. LKLF: A transcriptional regulator of single-positive T cell quiescence and survival. *Science* 277, 1986–90 (1997).

20. Solvason, N. et al. Induction of cell cycle regulatory proteins in anti-immunoglobulin-stimulated mature B lymphocytes. *J Exp Med* 184, 407–17 (1996).

21. Marton, M. J. et al. Drug target validation and identification of secondary drug target effects using DNA microarrays. *Nat Med* 4, 1293–301 (1998).

22. Dolmetsch, R. E., Lewis, R. S., Goodnow, C. C. & Healy, J. I. Differential activation of transcription factors induced by Ca2+ response amplitude and duration. *Nature* 386, 855–8 (1997).

23. Alessi, D. R., Cuenda, A., Cohen, P., Dudley, D. T. & Saltiel, A. R. PD 098059 is a specific inhibitor of the activation of mitogen-activated protein kinase in vitro and in vivo. *J Biol Chem* 270, 27489–94 (1995).

24. Iida, S. et al. Deregulation of MUM1/IRF4 by chromosomal translocation in multiple myeloma. *Nat Genet* 17, 226–30 (1997).

25. Langdon, W. Y., Harris, A. W., Cory, S. & Adams, J. M. The c-myc oncogene perturbs B lymphocyte development in E-mu-myc transgenic mice. *Cell* 47,11–8 (1986).

26. Svaren, J. et al. NAB2, a corepressor of NGFI-A (Egr-1) and Krox20, is induced by proliferative and differentiative stimuli. *Mol Cell Biol* 16, 3545–53 (1996).

27. Pfisterer, P. et al. CRISP-3, a protein with homology to plant defense proteins, is expressed in mouse B cells under the control of Oct2. *Mol Cell Biol* 16, 6160–8 (1996).

28. Slemmon, J. R. et al. Camstatins are peptide antagonists of calmodulin based upon a conserved structural motif in PEP-19, neurogranin, and neuromodulin. *J Biol Chem* 271, 15911–7 (1996).

29. Healy, J. I., Dohnetsch, R. E., Lewis, R. S. & Goodnow, C. C. Quantitative and qualitative control of antigen receptor signaling in tolerant B lymphocytes. *Novartis Found Symp* 215, 137–44 (1998).

30. Adachi, T., Flaswinkel, H., Yakura, H., Reth, M. & Tsubata, T. The B cell surface protein CD72 recruits the tyrosine phosphatase SHP-1 upon tyrosine phosphorylation. *J Immunol* 160, 4662–5 (1998).

31. Tyagi, S. & Kramer, F. R. Molecular beacons: probes that fluoresce upon hybridization. *Nat Biotechnol* 14, 303–8 (1996).

32. Mason, D. Y., Jones, M. & Goodnow, C. C. Development and follicular localization of tolerant B lymphocytes in lysozyme/anti-lysozyme IgM/IgD transgenic mice. *Int Immunol* 4, 163–75 (1992).

Although the foregoing invention has been described in detail for purposes of clarity of understanding, it will be obvious that certain modifications can be practiced within the scope of the appended claims. All publications and patent documents cited above are hereby incorporated by reference in their entirety for all purposes to the same extent as if each were so individually denoted.

What is claimed is:

1. A method of screening drug candidates, comprising:

a) providing a B cell that expresses one or more expression profile genes selected from the group consisting of carb anh II, IgD, CD72, SATB1, ApoE, CD83, cyclin D2, Cctq, MEF-2C, TGIF, Aeg-2, 1ck, E2-20K, pcp-4, kappa V, neurogranin, NAB2, gfi-1 hIP-30, TRAP, bmk, CD36, Evi-2, vimetin, Ly6E.1 and c-fes;

b) adding a drug candidate to the B cell;

c) determining the expression level of at least one gene of the expression profile genes in the B cell;

d) comparing the expression level of the at least one gene in the B cell with the expression level of the at least one gene in a control cell not contacted with the drug candidate to determine (i) whether expression of carb anh II, CD72, SATB1, ApoE, CD83, cyclin D2, Cctg, MEF-2C, TGIF, Aeg-2, 1ck, E2-20K, pcp-4, kappa V, neurogranin, NAB2 and/or gfi-1 is increased in the B cell relative to a control cell not contacted with the drug candidate, or (ii) whether expression of Ly6E.1, vimentin. hIP-30, TRAP, bmk, CD36, Evi-2 and/or c-fes is decreased in the B cell relative to the control cell; and e) identifying the drug candidate as a potential modulator of B cell tolerance if the expression level of a gene listed in (i) is increased and/or the expression level of a gene listed in (ii) is decreased.

2. The method according to claim 1, further comprising performing a binding assay to determine if the drug candidate identified in step e) binds to the protein encoded by the at least one gene.

3. The method according to claim 1, further comprising performing an assay to determine if the drug candidate identified in step e) modulates an activity of the protein encoded by the at least one gene.

4. The method according to claim 1, wherein the expression levels of a plurality of expression profile genes are determined and compared.

5. The method according to claim 4, wherein the expression levels of at least three expression profile genes are determined and compared.

6. The method according to claim 5, wherein the expression levels of at least five expression profile genes are determined and compared.

7. The method of claim 1, wherein the expression level is determined from the amount of transcript expressed by the at least one gene.

8. The method of claim 1, wherein the expression level is determined from the amount of protein expressed by the at least one gene.

* * * * *

UNITED STATES PATENT AND TRADEMARK OFFICE
CERTIFICATE OF CORRECTION

| | | |
|---|---|---|
| PATENT NO. | : 6,913,882 B2 | Page 1 of 1 |
| APPLICATION NO. | : 09/747760 | |
| DATED | : July 5, 2005 | |
| INVENTOR(S) | : Glynne et al. | |

It is certified that error appears in the above-identified patent and that said Letters Patent is hereby corrected as shown below:

Col. 1, line 3, insert:

-- FEDERALLY-SPONSORED RESEARCH OR DEVELOPMENT

This invention was made with Government support under contract AI019512 awarded by the National Institutes of Health. The Government has certain rights in this invention. --

Signed and Sealed this
Ninth Day of August, 2011

David J. Kappos
*Director of the United States Patent and Trademark Office*